(12) United States Patent
Nagai et al.

(10) Patent No.: US 6,662,115 B2
(45) Date of Patent: Dec. 9, 2003

(54) METHOD FOR COMPARISON OF DNA BASE SEQUENCES

(75) Inventors: Keiichi Nagai, Higashiyamato (JP); Ryotaro Irie, Urawa (JP); Susumu Hiraoka, Kokubunji (JP); Naoko Kasahara, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/050,010

(22) Filed: Mar. 30, 1998

(65) Prior Publication Data

US 2001/0010903 A1 Aug. 2, 2001

(30) Foreign Application Priority Data

Mar. 31, 1997 (JP) ............................................. 09-079586

(51) Int. Cl.[7] .......................... G06F 19/00; G01N 33/48; C12Q 1/68
(52) U.S. Cl. ............................... 702/20; 435/6; 702/27; 702/19
(58) Field of Search ............................. 435/6; 436/501; 702/19, 27, 20

(56) References Cited

PUBLICATIONS

States et al., Proceedings of the National Academy of Sciences (USA), vol. 88, pp. 5518–5522, 1991.*
Biotechnology Textbook Series 11, "Introduction of Computer in Biotechnology" H. Nakamura et al, Corona Publishing Co., 1995, pp. 141–143.
Journal of Molecular Biology, vol. 147, "Identification of Common Molecular Sequences", 1981, pp. 195–197.
J. Hein, "An Algorithm Combining DNA and Protein Alignment", J. Theor. Biol., No. 167, 1994, pp. 169–174.
J. Hein et al, "Genomic Alignment", Journal of Molecular Evolution, vol. 38, No. 3, Mar. 1994, pp. 310–316.
Birney, Ewan et al, "PairWise and SearchWise: finding the optimal alignment in a simultaneous comparison of a protein profile against all DNA translation frames", Nucleic Acids Research, vol. 24, No. 14, 1996, pp. 2730–2739.
Guan, Xiaojun et al, "Alignments of DNA and protein sequences containing frameshift errors", CABIOS, vol. 12, No. 1, 1996, pp. 31–40.
Uchimiya, Hirohumi et al, "Massive analysis of Paddy cDNA", PNE, vol. 37, No. 7, 1992, pp. 1364–1368.

* cited by examiner

*Primary Examiner*—Ardin H. Marschel
(74) *Attorney, Agent, or Firm*—Mattingly, Stanger & Malur, P.C.

(57) ABSTRACT

A method for comparing DNA base sequences by comparing similarities between two amino acid sequences translated from two DNA base sequences, respectively, includes (1) a step of dividing each of the first DNA base sequence and the second DNA base sequence into groups of successive three nucleotides each, translating each of these groups of nucleotides into an amino acid, and thereby obtaining a first amino acid sequence and a second amino acid sequence, and (2) a step of determining similarities between each amino acid of the first translated amino acid sequence and each amino acid of the second translated amino acid sequence in view of nucleotide insertions or deletions in the first and second DNA base sequence and amino acid insertions or deletions in the first and second translated amino acid sequence. The method is repeated by shifting the base sequences one base at a time.

3 Claims, 18 Drawing Sheets

(FIRST TRANSLATION METHOD)

| FIRST POSITION (5' END) | SECOND POSITION | | | | THIRD POSITION (3' END) |
|---|---|---|---|---|---|
| | T | C | A | G | |
| T | Phe(F) | Ser(S) | Tyr(Y) | Cys(C) | T |
| | Phe(F) | Ser(S) | Tyr(Y) | Cys(C) | C |
| | Leu(L) | Ser(S) | TERMINATION | TERMINATION | A |
| | Leu(L) | Ser(S) | TERMINATION | Trp(W) | G |
| C | Leu(L) | Pro(P) | His(H) | Arg(R) | T |
| | Leu(L) | Pro(P) | His(H) | Arg(R) | C |
| | Leu(L) | Pro(P) | Gln(Q) | Arg(R) | A |
| | Leu(L) | Pro(P) | Gln(Q) | Arg(R) | G |
| A | Ile(I) | Thr(T) | Asn(N) | Ser(S) | T |
| | Ile(I) | Thr(T) | Asn(N) | Ser(S) | C |
| | Ile(I) | Thr(T) | Lys(K) | Arg(R) | A |
| | Met(M) | Thr(T) | Lys(K) | Arg(R) | G |
| G | Val(V) | Ala(A) | Asp(D) | Gly(G) | T |
| | Val(V) | Ala(A) | Asp(D) | Gly(G) | C |
| | Val(V) | Ala(A) | Glu(E) | Gly(G) | A |
| | Val(V) | Ala(A) | Glu(E) | Gly(G) | G |

(FIRST TRANSLATION METHOD)

FIG. 7
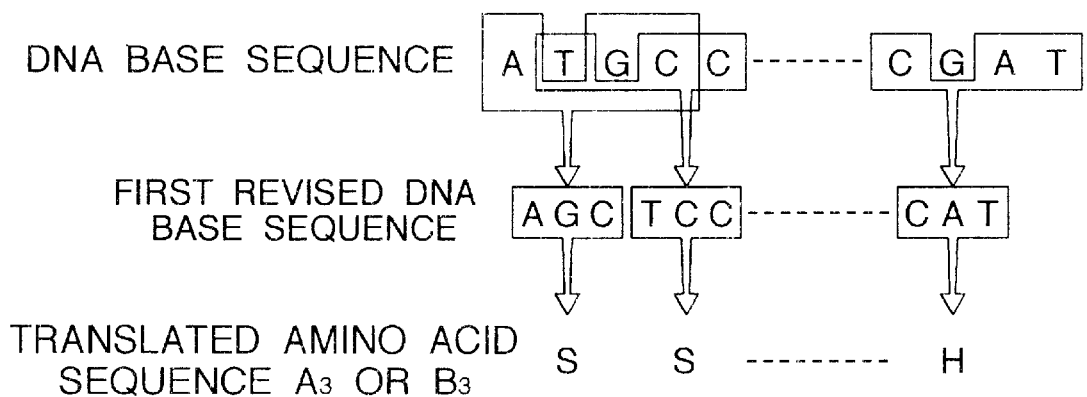
(SECOND TRANSLATION METHOD)
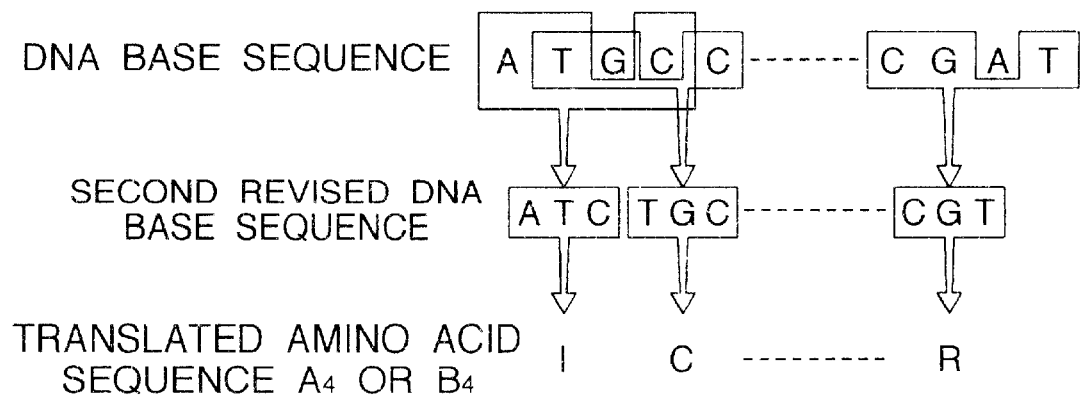
(THIRD TRANSLATION METHOD)

FIG. 9

THIRD AMINO ACID SEQUENCE

FOURTH AMINO ACID SEQUENCE i-3, j-4 i, j

FIG. 10

FIFTH AMINO ACID SEQUENCE

SIXTH AMINO ACID SEQUENCE i-3, j-4 i, j

FIG. 11

SEVENTH AMINO ACID SEQUENCE

EIGHTH AMINO ACID SEQUENCE i−4, j−3 i, j

FIG. 12

NINTH AMINO ACID SEQUENCE

TENTH AMINO ACID SEQUENCE i−4, j−3 i, j

FIG. 13

| | | | |
|---|---|---|---|
| (1) | $A_{i-3}$ $B_{j-3}$ | $A_i$ $B_j$ | |
| (2) | $A_i$ $B_{j-3}$ | --- $B_j$ | |
| (3) | $A_{i-3}$ $B_j$ | $A_i$ --- | |
| (4) | $A_{i-5}$ $B_{j-6}$ | a-a $B_{j-3}$ | $A_i$ $B_j$ |
| (5) | $A_{i-6}$ $B_{j-5}$ | $A_{i-3}$ b-b | $A_i$ $B_j$ |
| (6) | $A_{i-4}$ $B_{j-3}$ | a | $A_i$ $B_j$ |
| (7) | $A_{i-3}$ $B_{j-4}$ | b | $A_i$ $B_j$ |
| (8) | $A_{i-7}$ $B_{j-6}$ | a a a a $B_{j-3}$ | $A_i$ $B_j$ |
| (9) | $A_{i-6}$ $B_{j-7}$ | $A_{i-3}$ b b b b | $A_i$ $B_j$ |

FIG. 14

| (1) EXAMPLE OF ALIGNMENT IN THE CASE OF $H_1(i,j)$ | (2) EXAMPLE OF ALIGNMENT IN THE CASE OF $H_2(i,j)$ |
|---|---|
| ACG<br>Thr<br>Lys<br>AAG | ACG<br>Thr<br>-<br>--- |
| (3) EXAMPLE OF ALIGNMENT IN THE CASE OF $H_3(i,j)$ | (4) EXAMPLE OF ALIGNMENT IN THE CASE OF $H_4(i,j)$ |
| ---<br>-<br>Lys<br>AAG | ACGCTT<br>ThrLeu<br>* Leu<br>A-GCTT |
| (5) EXAMPLE OF ALIGNMENT IN THE CASE OF $H_5(i,j)$ | (6) EXAMPLE OF ALIGNMENT IN THE CASE OF $H_6(i,j)$ |
| A-GCTT<br>* Leu<br>LysLeu<br>AAGCTT | TACG<br>Thr<br>Lys<br>-AAG |

| (7) EXAMPLE OF ALIGNMENT IN THE CASE OF $H_7(i,j)$ |
|---|
| -ACG<br>Thr<br>Lys<br>TAAG |
| (8) EXAMPLE OF ALIGNMENT IN THE CASE OF $H_8(i,j)$, $H_9(i,j)$ |
| ACCTCTT<br>T trLeu<br>S erLeu<br>A-GTCTT |
| (9) EXAMPLE OF ALIGNMENT IN THE CASE OF $H_{10}(i,j)$, $H_{11}(i,j)$ |
| AC-TCTT<br>Th rLeu<br>Se rLeu<br>AGGTCTT |

FIG. 15

```
Query sequence: T88509    12205 Arabidopsis thaliana cDNA clone
Target sequence:RICC0812A   Rice cDNA, partial sequence (C0812A).
Score: 125   Query length(dir): 456(0)   Target length(dir): 336(0)
Alignment region   Query:     85    338
                   Target:    76    335
                                                        e
Query:  ttcattcatccgtngttccccagctc aatcagtctc gttcccttccatcagccaacac
        PheIleHisPro***PheProSerSer AsnA rgLeu ArgSerLeuProSerAlaAsnTh
          :   .   :          :        :     :    :   .   :       :
        PheLeuAsnProAlaArgProLeuLeu ArgA rgPro ArgAlaLeuProSerLeuValTh
Target: ttcctaaacccggcgcggccattgctc cggc-gacca gagcccttccttcattggttac
             c          b'
Query:  acaatccctc ttcggtctc aatca ggc------ ccgctcgtggtggacgtgtcacagc
        rGlnSerLeu PheGlyLeu LysSer Gly  -  - ThrAlaArgGlyGlyArgValThrAl
          :   :     :        :      :            .           :   :   .
        rGlnSerLys His * Asn MetSer GlyLeuArg IleSerAsnLysPheArgValSerAl
Target: gcaaagcaaa catt-gaac tgtca ggcctaagg tctccaacaagttcaggtgtccgc
                                                 b
Query:  catggctacatacaaggtcaagttcatcacaccaga ggt---gagctagaggttgagtg
        aMetAlaThrTyrLysValLysPheIleThrProGlu Gly - GluLeuGluValGluCy
          .   :             :   :   :   :   . :    :    :    :    :
        aThrGly***HisLysValLysLeuIleGlyProAsp GlyVal GluHisGluPheGluAl
Target: gacaggtngtcacaaggtaaagcttataggcccgga ggtgtc gagcacgagtttgaagc
                                                         d
Query:  tgacgncgncgtctacgttcttnatgctgctgaggaagctgga atcgatt tgccttact
        sAsp******ValTyrValLeu***AlaAlaGluGluAlaGly Ile IleLeuProTyrS
          :   .   :           :    :         :   .    :        :   :
        aProGluAspThrTyrIleLeuGluAlaAlaGluThrAlaGly Val *LeuPro*
Target: ccctgaagatacctacattctcgaggccgctgaaactgcgggg gtg-gng tgccattnt Query:  cttgccgtgctggttcttgttcg
        erCysArgAlaGlySerCysSer
          :   :   :   :   :   :   :
        **CysArgAlaGlySerCysSer
Target: natgccgtgctggatcatgctcc
```

FIG. 16

```
Query sequence: T88643    12339 Arabidopsis thaliana cDNA clone
Target sequence:RICC10428A    Rice cDNA, partial sequence (C10428_1A).
Score: 107    Query length(dir): 595(0)    Target length(dir): 314(0)
Alignment region    Query:    35    292
                    Target:   65    313

Query:    atggcgaattccggcgaagagaagttgaagctctactcttactggagaagctcgtgtgct
          MetAlaAsnSerGlyGluGluLysLeuLysLeuTyrSerTyrTrpArgSerSerCysAla
          :   :       :   :   .   :         :       :           :       :
          MetAlaGlySerGlyAspGlu  -  LeuMetLeuLeuGlyLysTrpProSerProPheVal
Target:   atggccggatcaggagacgag---ctgatgctgctcggcaaatggccaagcccattcgtc Query:    catcgtgtccgtatcgccctcgctttgaaagggcttgattatnagtatataccagtgaat
          HisArgValArgIleAlaLeuAlaLeuLysGlyLeuAspTyr***TyrIleProValAsn
              :       .   :       :   :   :       :   :   .       .
          ThrArgValGluLeuAlaLeuGlyLeuLysGlyLeuSerTyrGluTyrValLysGlnAsp
Target:   accagggttgagctcgcgctcggcctcaagggcctcagctacgagtacgtcaagcaggac Query:    ttnctcaagggtgatcaattcgattcanatttcaagaagatcaatccaatgggaactgta
          *LeuLysGlyAspGlnPheAspSer*PheLysLysIleAsnProMetGlyThrVal
                .                       .                       .           .
          LeuValAsnLysSerGluLeuLeuLeuAlaSerAsnProValHisLysLys  -  -  Ile
Target:   ctcgtcaacaagagcgagctcctcctcgcctccaacccggtgcacaagaag------atc Query:    ccagctctggtggatggagatgttgtgattaatgattcttttgcgataataatgtatctg
          ProAlaLeuValAspGlyAspValValIleAsnAspSerPheAlaIleIleMetTyrLeu
              :       :   .                   .       .   :           :       :   .
          ProValLeuIleHisAsnGlyLysProValCysGluSerSerIleIleValGlnTyrIle
Target:   cccgtgctcatccacaacggcaagccggtctgcgagtcgtcaatcatcgtgcagtacatc Query:    gatgagaagtaccctgag
          AspGluLysTyrProGlu
          :   :       .   :   .
          AspGluAlaPheProAsp
Target:   gacgaggccttccccgac
```

FIG. 17

```
Query sequence: T88476    12172 Arabidopsis thaliana cDNA clone
Target sequence:RICS5087A    Rice cDNA, partial sequence (S5087_1A).
Score: 101    Query length(dir): 260(0)   Target length(dir): 494(0)
Alignment region    Query:     43    228
                    Target:   261    448

Query:   ggaagagctccatgctgcgacaaggcaaacntgaagaaaggaccatggtcaccggaagan
         GlyArgAlaProCysCysAspLysAlaAsn***LysLysGlyProTrpSerProGlu***
          :  :       :  :         :     . :  :        :  :       :
         GlyArgHisSerCysCysTyrLysGlnLysLeuArgLysGlyLeuTrpSer***GluGlu
Target:  gggagacattcctgctgctacaagcagaagctgaggaagggctctggtcanctgaggag Query:   gatg-tgaagctcaaggtttacatcgacaaatatggcactggtggcaactggttcgcact
         Asp  *  GluAlaGlnGlyLeuHisArgGlnIleTrpHisTrpTrpGlnLeuValArg Le
          :      :    :    :    :    :    :    :    :    :    :    :
         AspGluGluAlaHisGlyProHisAsnGlnAlaTrp***TrpLeuLeuGlyHisArg Ph
Target:  gatgaggaagctcatggaccacataaccaagcatggncatggctgctggggcaccgt-tt Query:   gcctcagaaanttggnctgaagagatgt-ggtaaganttgcagactgaga-tggcttaat
         uProGlnLys****LeuLysArgCys GlyLys*CysArgLeuArg TrpLeuAsn
              :  :         :        :        :  :  :  :  :
         eGlnAsnLeuGlnGlyPheGlnArgCys AlaLysAlaPheArgLeuArg Trp***Asn
Target:  ccaaaacttgcaggggtttcagagatgtngcaaaagctttcaggctgaggttgggtnaac Query:   tncttaaga
         ***LeuArg
            :  :
         TyrLeuArg
Target:  tacttgagg
```

METHOD FOR COMPARISON OF DNA BASE SEQUENCES

BACKGROUND OF THE INVENTION

1. Field of the Invention

The present invention relates to a method for comparing of DNA base sequences and a method for searching for DNA base sequences. In particular, it relates to a method for high-sensitivity detection of similarities between DNA base sequences and a method for estimation of an amino acid sequence coded for by a DNA base sequence.

2. Description of the Related Art

In recent years, there has been the following increasing trend: the DNA base sequences of various organisms are determined and the function of a protein coded by each DNA base sequence is analyzed. The DNA base sequence is a sequence of four kinds of bases A, C, G and T, and portions of the DNA base sequence code for biofunctional proteins, respectively. Of these proteins, those having an important function can be utilized, for example, for design and development of drugs, and there is desired a technique for accurately estimating the function of the protein coded for by the DNA base sequence. In general, the determination of the DNA base sequence is technically easier than experimental protein sequencing.

The function of a protein coded by a newly determined DNA base sequence is estimated as follows: the DNA base sequence is translated into an amino acid sequence (which permits protein sequencing) by using the well-known codon table (each of the starting point of translation into amino acids, the terminating point of translation into amino acids and the kinds of amino acids are prescribed in terms of a triplet nucleotide unit (a codon unit)), and the result of the protein sequencing is compared with data on a protein having a known function, to judge whether the proteins are similar or not.

In a DNA base sequence, the exon region coding for protein information is a region to be translated into amino acids. The codons are unequivocally translated into the amino acids. When the direction of translation of the DNA base sequence and the translation starting point are known, the DNA base sequence can be translated into an amino acid sequence, i.e., a protein by picking out triplets of successive nucleotides from the DNA base sequence in succession. However, if there is an error due to a nucleotide insertion or deletion in the DNA base sequence, the exon region of the DNA base sequence is shifted. Since the DNA base sequence is translated into amino acids as codon units, it is translated into completely different amino acids if a nucleotide insertion or deletion is present.

For comparing two DNA base sequences by translating them into amino acid sequences, respectively, and comparing these translated amino acid sequences, the translated amino acid sequences should be determined from the respective DNA base sequences.

FIG. 1 is a diagram illustrating 6 kinds of reading frames in a DNA base sequence in the translation of the DNA base sequence into an amino acid sequence [(first prior art): for example, reference 1: Biotechnology textbook series 11 "Introduction of Computer in Biotechnology" written by Haruki Nakamura and Kenta Nakai, pp. 66–67 (1995), CORONA PUBLISHING CO., LTD., Tokyo, Japan)].

The 6 kinds of the reading frames are as follows:

Frame (1): a frame according to which a DNA base sequence is translated into an amino acid sequence as codon units from the 5'-terminal of the DNA base sequence.

Frame (2): a frame according to which the DNA base sequence is translated into an amino acid sequence as codon units while shifting the starting position of each codon by one base from that in frame (1).

Frame (3): a frame according to which the DNA base sequence is translated into an amino acid sequence as codon units while shifting the starting position of each codon by two bases from that in frame (1).

Frame (4): a frame according to which the translation of a sequence complementary to the DNA base sequence into an amino acid sequence as codon units is initiated from the 5'-terminal of the complementary sequence.

Frame (5): a frame according to which the complementary sequence is translated into an amino acid sequence as codon units while shifting the translation starting position by one base from that in frame (4).

Frame (6): a frame according to which the complementary sequence is translated into an amino acid sequence as codon units while shifting the translation starting position by two bases from that in frame (4).

From frame (1) to frame (3), the translation starting position is shifted base by base from the 5'-terminal. From frame (4) to frame (6), the translation starting position is shifted base by base from the 5'-terminal of the sequence complementary to the original DNA base sequence (the 3'-terminal of the original DNA base sequence). Therefore, there are the six kinds of reading frames (1) to (6). A DNA base sequence is translated into an amino acid sequence by employing each of frames (1) to (6). Amino acid sequences translated from two DNA base sequences, respectively, by employing the same frame are compared. Thus, 6 kinds, in all, of amino acid sequences translated from one of the DNA base sequences are compared from those translated from the other DNA base sequence.

As a typical program for searching similar sequences, there is widely known BLAST developed by Altshul et al. of NCBI, a branch of U.S. NIH, the source program of which has been disclosed (see, for example, the first reference, pages 141 to 143). The BLAST family includes BLASTN for comparing DNA base sequences, BLASTP for comparing amino acid sequences, BLASTX for searching for each of 6 kinds of amino acid sequences mechanically translated from a DNA base sequence according to each of the above-mentioned 6 kinds of frames, by using an amino acid sequence data base, and TBLASTX for mechanically translating each of a query DNA base sequence as a first DNA base sequence and a DNA base sequence read out of a DNA base sequence data base (a target DNA base sequence) as a second DNA base sequence according to each of the above-mentioned 6 kinds of the frames, and comparing 36 combinations of 6 kinds of amino acid sequences translated from the first DNA base sequence and 6 kinds of amino acid sequences translated from the second DNA base sequence. In the case of the BLAST family, high-speed pattern matching of a base sequence having a definite length in a query DNA base sequence with a target DNA base sequence was carried out at first, and a region similar to the query DNA base sequence is detected on the basis of the position of a base sequence with a definite length detected in the target DNA base sequence.

In the Smith-Waterman method, each base of a query DNA base sequence is compared with each base of a target DNA base sequence, a score (a similarity) suitable for the combination of the two bases is given, the scores (similarities) thus given are accumulated, and there is sought a path (an alignment) in which the accumulated score (similarity) becomes maximum [(third prior art): for example, reference 2: "Identification of Common Molecular Subsequences", J. Mol. Biol.,147 (1981), pp. 195–197].

In the third prior art, the combinations of two bases of two DNA base sequences, respectively, are compared by a dynamic programming method, and scores between the two DNA base sequences are determined. When a DNA base sequence similar to a specific noted DNA base sequence (hereinafter referred to as "query DNA base sequence" or "first DNA base sequence") is searched for in a DNA base sequence data base, a matrix is formed by aligning the bases of the query DNA base sequence (number of bases: M) in regular order from the 5'-terminal along a first axis (for example, x-axis) and the bases of a DNA base sequence (number of bases: N) read out of the DNA base sequence data base (hereinafter referred to as "target DNA base sequence" or "second DNA base sequence") in regular order from the 5'-terminal along a second axis (for example, y-axis) (in the present specification, such a matrix is hereinafter referred to "score matrix") (FIG. 2).

FIG. 2 is a diagram illustrating accumulation paths of scores for comparing the first and second DNA base sequences. Each combination of the two bases of the first and second DNA base sequences, respectively, is expressed as the position of a score matrix element (i, j) (i=1, 2, - - - , M; j=1, 2,- - - , N).

In the dynamic programming method, shift paths (search paths) in three directions, the vertical direction, the horizontal direction and the bias direction (the directions a, b and c, respectively, shown in FIG. 2) to a score matrix element (i, j) are considered, and the position of (i, j) is shifted toward a score matrix element (M, N) at the lower right corner from the score matrix element (1, 1) at the upper left corner shown in FIG. 2, by changing the number i from 1 to M and the number j from 1 to N, whereby there is determined the optimum path (the optimum alignment) which shows the optimum combinations for similarities of the bases of the first DNA base sequence and the bases of the second DNA base sequence.

The value H(i, j) of a score matrix element (i, j) indicates an accumulated similarity (score) between a base sequence from the first base to the i-th base in the first DNA base sequence and a base sequence from the first base to the j-th base in the second DNA base sequence. For the shift paths in the directions a, b and c shown in FIG. 2, the accumulated similarities (scores), $H_a(i, j)$, $H_b(i, j)$ and $H_c(i, j)$, respectively, are defined by the (equation 1), (equation 2) and (equation 3) shown below, by using a score s(i, j) indicating the similarity between the i-th base of the first DNA base sequence and the j-th base of the second DNA base sequence, a gap penalty score p and accumulated similarities (scores) H(i−1, j−1), H(i−1, j) and H(i, j−1) at score matrix elements (i−1, j−1), (i−1, j) and (i, j−1), respectively, at the original points before shift to the point (i, j). The maximum among $H_a(i, j)$, $H_b(i, j)$ and $H_c(i, j)$ [(equation 4)] is selected as H(i, j). The above-mentioned score s(i, j) can be determined using a previously stored score table. For example, a score of 4 is given to a combination of the same bases, a score of −8n−4 is given when the number of inserted or deleted nucleotides is n, and a score of −3 is given to a combination of two different bases.

$H_a(i, j)=H(i-1, j-1)+s(i, j)$ (equation 1)

$H_b(i, j)=H(i, j-1)+p$ (equation 2)

$H_c(i, j)=H(i-1, j)+p$ (equation 3)

$H(i, j)=\max\{H_a(i, j), H_b(i, j), H_c(i, j)\}$ (equation 4)

The gap penalty score p added in the shift path b corresponds to the presence of a nucleotide deletion after the i-th base of the first DNA base sequence, and the gap penalty score p added in the shift path c corresponds to the presence of a nucleotide deletion after the j-th base of the second DNA base sequence.

The first and second DNA base sequences are compared by varying the number i from 1 to M and the number j from 1 to N in shift paths from the score matrix element (1, 1) to the score matrix element (M, N), and scores or gap penalty scores are added up in each shift path, whereby there is determined H*=H(M, N), the maximum accumulated similarity (score) between the whole first DNA base sequence and the whole second DNA base sequence. Consequently, it is possible to determine an alignment which gives the greatest similarity between the first and second DNA base sequences, namely, the optimum alignment showing the optimum combinations of the bases of the first DNA base sequence and the bases of the second DNA base sequence.

The third prior art is applicable not only to the investigation of similarities between two DNA base sequences but also to the investigation of similarities between two amino acid sequences.

SUMMARY OF THE INVENTION

The above-mentioned first prior art involves the following problem. When a nucleotide insertion or deletion is present in a DNA base sequence, a frame shift occurs at the position of the nucleotide insertion or deletion, and an amino acid sequence coded for by the portion of the base sequence after the frame shift position does not have any similarity which would be given if there were no nucleotide insertion or deletion. Therefore, an amino acid sequence cannot be found which would be obtainable if there were no nucleotide insertion or deletion. Thus, a miss of omission occurs in the search.

Even if an amino acid sequence very similar to an amino acid sequence obtained by translation using, for example, the frame (1) among the 6 kinds of the frames in a DNA base sequence is present in an amino acid sequence translated from another DNA base sequence, the following problem is caused when a nucleotide insertion or deletion is present in the DNA base sequence: the position of the frame is changed to that of the frame (2) or the frame (3) in the portion of the base sequence after the position of the nucleotide insertion or deletion. In the prior art, there has been disclosed neither a method for comparison of DNA base sequences nor a method for search for DNA base sequences, which has been developed in view of a change of reading frame caused by a nucleotide insertion or deletion in the DNA base sequence.

The BLAST family including TBLASTX in the above-mentioned second prior art is disadvantageous in that a miss of omission occurs in the search because gaps due to nucleotide insertions or deletions in a DNA base sequence or amino acid insertions or deletions in an amino acid sequence are not considered for assuring high-speed calculation.

The above-mentioned third prior art is an accurate search method but is disadvantageous in that it requires a long period of time because each base of a DNA base sequence is compared with each base of another DNA base sequence. When the third prior art is combined with the first prior art, namely, each of two DNA base sequences, a quetry DNA base sequence and a target DNA base sequence is translated into an amino acid sequence and the translated amino acid sequences are compared, a longer search time is required because it is necessary to compare 36 combinations of 6 kinds of amino acid sequences translated from the first DNA base sequence according to the 6 kinds of the frames, respectively, explained in the first prior art and 6 kinds of amino acid sequences translated from the second DNA base sequence according to the 6 kinds of the frames, respectively.

Moreover, when the Smith-Waterman method as the third prior art is combined with the first prior art, the insertion or deletion of amino acids or the insertion or deletion of nucleotides as codon unit in a DNA base sequence can be considered, but the insertion or deletion of nucleotides in a number other than multiples of 3 (i.e. the number of nucleotides constituting a codon unit) in a DNA base sequence cannot be considered. Therefore, the change of the position of frame cannot be considered.

In the prior arts, there is not considered the prevention of the production of erroneous results due to nucleotide insertions or deletions in a DNA base sequence. That is, it is not considered that the DNA base sequence is translated into an amino acid sequence in view of the presence of the nucleotide insertions or deletions.

Japanese Patent Application No. 7-265157 [reference 3: application date in Japan: Oct. 13, 1995 (JP-A-09-105748 (laid-open date in Japan: Apr. 22, 1997))] which is not a known reference discloses a method for comparison of DNA base sequences which comprises dividing each of first and second DNA base sequences into triplets of successive nucleotides, to form first and second, respectively, intermediate DNA base sequences, translating each of the first and second intermediate DNA base sequences into amino acids to form first and second, respectively, translated amino acid sequences, determining a first similarity between the first DNA base sequence and the first intermediate DNA base sequence, a second similarity between the second DNA base sequence and the second intermediate DNA base sequence, and a third similarity between the first translated amino acid sequence and the second translated amino acid sequence, and choosing the first and second intermediate DNA base sequences and the first and second translated amino acid sequences so that a parameter obtained from the first, second and third similarities by the use of a predetermined function may be maximum.

Japanese Patent Application No. 8-167770 (reference 4: application date in Japan: Jun. 27, 1996) which is not a known reference discloses a method for comparison of sequences which comprises translating a query DNA base sequence into amino acids in view of nucleotide insertions or deletions, comparing the resulting translated amino acid sequence with a target amino acid sequence read out of an amino acid data base, according to the Smith-Waterman method, determining the score (similarity) between the i-th amino acid of the translated amino acid sequence and the j-th amino acid of the target amino acid sequence in view of 7 kinds of paths, and thereby aligning the translated amino acid sequence with the target amino acid sequence.

The reference 3, however, does not disclose a technique concerning a specific example of path in calculation according to the dynamic programming method. The reference 4 discloses a method comprising picking out successive codons each having a starting position one or two bases after that of the preceding codon, in the translation of a query DNA base sequence into an amino acid sequence (which corresponds to the first translation method employed in the present invention), but does not disclose the second and third translation methods employed in the present invention which are explained hereinafter in detail. The reference 4 does not disclose a technique for comparing an amino acid sequence translated from a query DNA base sequence with an amino acid sequence translated from a DNA base sequence read out of a DNA base sequence data base.

An object of the present invention is to provide a method for comparison of DNA base sequences which hardly causes a miss or omission in search and comprises translating each of a query DNA base sequence and a DNA base sequence read out of a DNA base sequence data base (a target DNA base sequence) into an amino acid sequence, and thereby comparing the two DNA base sequences through the translated amino acid sequences, in particular, a method for high-sensitivity detection of similarities between DNA base sequences and a method for estimation of an amino acid sequences coded for by a query DNA base sequence.

In the method for comparison of DNA base sequences of the present invention, when similarities between first and second DNA base sequences are investigated, each DNA base sequence is first divided into triplets of successive nucleotides which may involve a nucleotide insertion or deletion. Each of the triplets is translated into an amino acid according to the codon table. Similarities between each amino acid of the thus obtained first translated amino acid sequence and each amino acid of the thus obtained second translated amino acid sequence are accumulated in view of amino acid insertions or deletions in each amino acid sequence to obtain an accumulated score (similarity). There are determined combinations of amino acids of the first translated amino acid sequence and those of the second translated amino acid sequence which give the maximum accumulated similarity (the maximum accumulated score). Thus, there are attained the maximum accumulated score, the alignment of the first and second translated amino acid sequences, and the alignment of the DNA base sequence corresponding to the first translated amino acid sequence with the DNA base sequence corresponding to the second translated amino acid sequence. A specific noted DNA base sequence (a query DNA base sequence) is used as the above first DNA base sequence, and a known DNA base sequence read out of any of various DNA base sequence data bases (a target DNA base sequence) is used as the above second DNA base sequence.

As a method for translating each DNA base sequence into an amino acid sequence which is adopted in the method for comparison of DNA base sequences of the present invention, the following first, second and third translation methods are employed in combination.

In the first translation method, the DNA base sequence is translated into an amino acid sequence according to a predetermined translation rule by codon table while shifting a reading frame for the DNA base sequence at every triplet of successive nucleotides base by base from the end of the DNA base sequence.

In the second translation method, a reading frame for the DNA base sequence is shifted at every quartet of successive nucleotides base by base from the end of the DNA base sequence, the second of the four nucleotides of each quartet is taken as an inserted nucleotide, and the DNA base sequence is translated into an amino acid sequence according to a predetermined translation rule by codon table by using the remaining three of the four nucleotides.

In the third translation method, a reading frame for the DNA base sequence is shifted at every quartet of successive nucleotides base by base from the end of the DNA base sequence, the third of the four nucleotides of each quartet is taken as an inserted nucleotide, and the DNA base sequence is translated into an amino acid sequence according to a predetermined translation rule by codon table by using the remaining three of the four nucleotides.

In the method for comparison of DNA base sequences of the present invention, a dynamic programming method is employed for calculating the accumulated score in the comparison of the first and second amino acid sequences translated from the first and second, respectively, DNA base sequences. In the calculation according to the dynamic programming method, when there are accumulated scores (similarities) between the i-th amino acid of the first translated amino acid sequence and the j-th amino acid of the second translated amino acid sequence which is represented by a score matrix element (i, j), there are considered seven paths from score matrix elements (i−3, j−3), (i, j−3k), (i−3k, j), (i−3n+1, j−3n), (i−3n, j−3n+1), (i−3m, j−3m−1) and (i−3m−1, j−3m), respectively, wherein k is an integer in a range of k≧1, m is an integer in a range of m≧1, and n is an integer in a range of n≧2. When k=1, m=1 and n=2, there are considered paths from score matrix elements (i−3, j−3), (i, j−3), (i−3, j), (i−5, j−6), (i−6, j−5), (i−3, j−4) and (i−4, j−3), respectively. The elements in the parentheses are positive numbers. The symbol i is an integer in a range of i≦M wherein M is the number of amino acids in the first translated amino acid sequence, and the symbol j is an integer in a range of j≦N wherein N is the number of amino acids in the second translated amino acid sequence.

According to the present invention, similarities between the DNA base sequences can be compared through the translated amino acid sequences. Therefore, the comparison can be carried out in detail by listing scores reflecting not only the agreement or disagreement of amino acids but also chemical characteristics (e.g. the hydrophilicity or hydrophobicity of amino acids) and physical characteristics (e.g. the size of amino acids) in a score table used for the comparison for the similarities. Thus, the sensitivity of search for the similarities between the DNA base sequences is enhanced.

Furthermore, misses or omissions in the search can be reduced because the comparison can be carried out in view of nucleotide insertions or deletions in the DNA base sequences and amino acid insertions or deletions in the translated amino acid sequences.

The method for comparison of DNA base sequences of the present invention is summarized as follows with reference to FIG. 3. Each of a query DNA base sequence and a DNA base sequence read out of a data base is translated into an amino acid sequence (304, 306), similarities between the translated amino acid sequences are calculated in view of nucleotide insertions or deletions and amino acid insertions or deletions, followed by score accumulation by a dynamic programming method (307), top accumulated scores and paths are calculated by the dynamic programming method, for two translated amino acid sequences giving the top accumulated scores which have been obtained by the similarity search (312), tracing of a path giving the maximum accumulated score is calculated (313), and the result of alignment of the translated amino acid sequences is displayed together with that of alignment of the DNA base sequences. Even if a nucleotide insertion or deletion is present in the two DNA base sequences to be compared, it becomes possible to determine similarities between the DNA base sequences through the translated amino acid sequences. Therefore, the sensitivity of search is enhanced.

BRIEF DESCRIPTION OF THE DRAWINGS

FIG. 4 shows an example of table of prior art prescribing scores to be given to combinations of two amino acids which is used in the embodiment of the present invention.

FIG. 5 shows a codon table of prior art prescribing the termination of translation into amino acids and the kinds of amino acids so that they may correspond to the triplet nucleotide units (codon units), respectively, in the codon table.

FIG. 7 is a diagram illustrating the second and third translation methods for translating a DNA base sequence into an amino acid sequence in the embodiment of the present invention.

Each of FIG. 9 and FIG. 10 is a diagram showing a point (i−3, j−4) at which scores $S_2$(i−3, j−4) and $S_3$(i−3, j−4) are determined in the embodiment of the present invention.

Each of FIG. 11 and FIG. 12 is a diagram showing a point (i−4, j−3) at which scores $S_4$(i−4, j−3) and $S_5$(i−4, j−3) are determined in the embodiment of the present invention.

FIG. 13 is a diagram showing general examples of alignment result corresponding to shift paths, respectively, in 9 directions in calculation by a dynamic programming method in the embodiment of the present invention.

FIG. 14 is a diagram showing specific examples of alignment result corresponding to the shift paths, respectively, in the 9 directions in calculation by the dynamic programming method in the embodiment of the present invention.

Each of FIG. 15 (SEQ ID NOS 1–4), FIG. 16 (SEQ ID NOS 5–8), and FIG. 17 (SEQ ID NOS 9–12) is a diagram showing an example of alignment result obtained by similarity search in the embodiment of the present invention.

Figure 18:
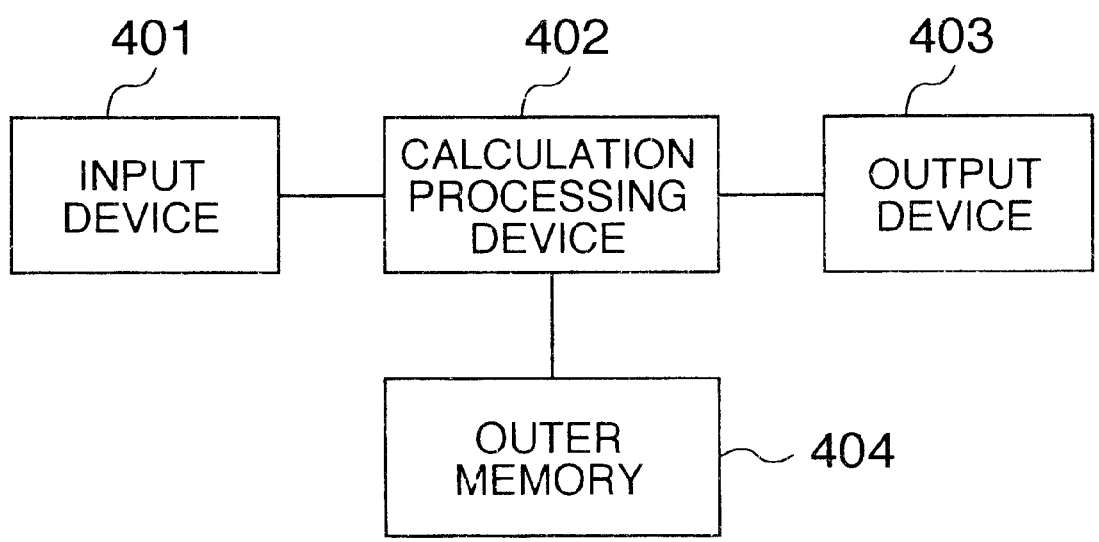

FIG. 18 is a diagram showing the structure of an apparatus for practicing the method for comparison of DNA base sequences of the present invention.

DESCRIPTION OF THE PREFERRED EMBODIMENTS

An examination is given below by taking the case of search for a query DNA base sequence by the use of a DNA base sequence data base.

Figure 3:
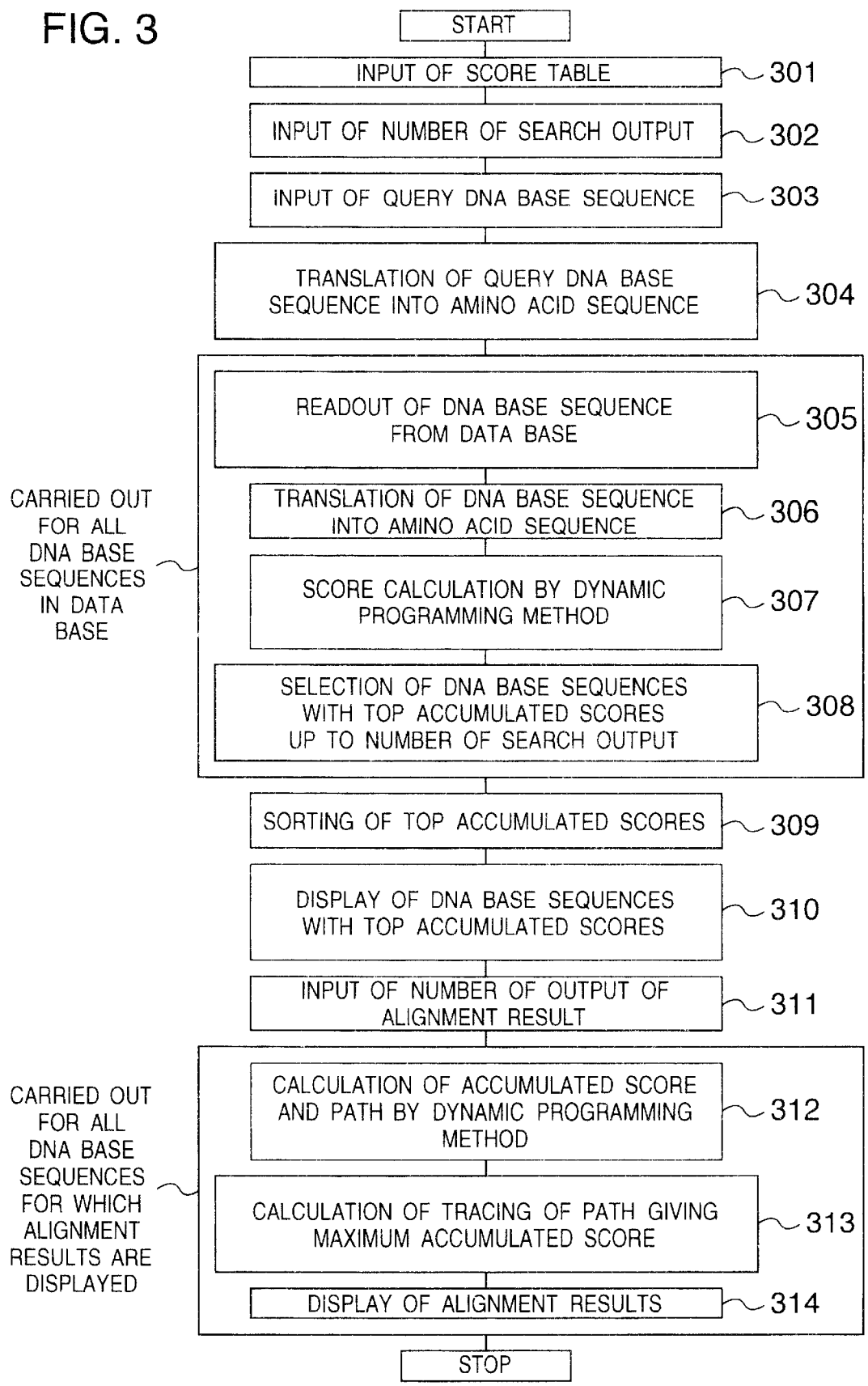
FIG. 3 is a flow chart illustrating an example of treating process in an embodiment of the present invention.

FIG. 3 is a flow chart illustrating an example of treating process in the embodiment of the present invention. The outline of a method for comparison of DNA base sequences as the embodiment of the present invention is explained below with reference to FIG. 3. First, (step 301) to (step 304) are carried out.

(Step 301): input of a score table prescribing the similarity of each combination of two amino acids.

(Step 302): input of the number of search output of DNA base sequences with top accumulated scores displayed in an output device as a result of search in a DNA base sequence data base.

(Step 303): input of a query DNA base sequence.

(Step 304): translated amino acid sequences $A_1$, $A_2$, $A_3$, $A_4$, $A_5$ and $A_6$ are obtained by translating each of the query DNA base sequence and a sequence complementary to the query DNA base sequence by each of the first, second and third translation methods explained hereinafter.

The translated amino acid sequence $A_1$ is obtained by translation from the query DNA base sequence by the first translation method. The translated amino acid sequence $A_2$ is obtained by translation from a sequence complementary to the query DNA base sequence by the first translation method. The translated amino acid sequence $A_3$ is obtained by translation from the query DNA base sequence by the second translation method. The translated amino acid sequence $A_4$ is obtained by translation from the query DNA base sequence by the third translation method. The translated amino acid sequence $A_5$ is obtained by translation from the sequence complementary to the query DNA base sequence by the second translation method. The translated amino acid sequence $A_6$ is obtained by translation from the sequence complementary to the query DNA base sequence by the third translation method.

Then, all target DNA base sequences to be read out of the DNA base sequence data base are subjected to the following steps (step 305) to (step 308).

(Step 305): the target DNA base sequences are read out of the DNA base sequence data base.

(Step 306): translated amino acid sequences $B_1$, $B_2$, $B_3$, $B_4$, $B_5$ and $B_6$ are obtained by translating each of the read-out target DNA base sequences and their complementary base sequences by each of the first, second and third translation methods explained hereinafter in detail.

The translated amino acid sequence $B_1$ is obtained by translation from the target DNA base sequence by the first translation method. The translated amino acid sequence $B_2$ is obtained by translation from a sequence complementary to the target DNA base sequence by the first translation method. The translated amino acid sequence $B_3$ is obtained by translation from the target DNA base sequence by the second translation method. The translated amino acid sequence $B_4$ is obtained by translation from the target DNA base sequence by the third translation method. The translated amino acid sequence $B_5$ is obtained by translation from the sequence complementary to the target DNA base sequence by the second translation method. The translated amino acid sequence $B_6$ is obtained by translation from the sequence complementary to the target DNA base sequence by the third translation method.

(Step 307): accumulated similarities between the translated amino acid sequences in each of the following 4 combinations of the 4 kinds of the translated amino acid sequences obtained in (step 304) and (step 306) is calculated by a dynamic programming method:

(a) the combination of the translated amino acid sequences $A_1$ and $B_1$, (b) the combination of the translated amino acid sequences $A_1$ and $B_2$, (c) the combination of the translated amino acid sequences $A_2$ and $B_1$, and (d) the combination of the translated amino acid sequences $A_2$ and $B_2$.

(Step 308): DNA base sequences with top accumulated scores up to the number of search output are selected, and information on the DNA base sequences with top accumulated scores is read out of the DNA base sequence data base and stored.

Next, all the DNA base sequences read out of the DNA base sequence data base are subjected to the following (step 309) to (step 311).

(Step 309): the accumulated similarities (scores) are lined up in order of decreasing value, and top accumulated scores corresponding to the number of search output are sorted.

(Step 310): the DNA base sequences with top accumulated scores are displayed in a display (403 in FIG. 18). In this case, the DNA base sequences with top accumulated scores may be output in an outer memory (404 in FIG. 18) such as a hard disc.

(Step 311): there is input the number of similarity search results (the number of output of alignment results) at which display of the alignment results is considered preferable, judging from the top accumulated scores displayed in (step 310).

Subsequently, all the target DNA base sequences for which the alignment results are displayed are subjected to following (step 312) to (step 314).

(Step 312): accumulated scores and paths are calculated by the dynamic programming method.

(Step 313): tracing of a path giving the maximum accumulated score is calculated to obtain an alignment result of two amino acid sequences translated from the query DNA base sequence and the target DNA base sequence read out of the DNA base sequence data base, respectively, and an alignment result of the DNA base sequences corresponding to the translated amino acid sequences, respectively.

(Step 314): the alignment result obtained in (step 313) is displayed in a display (403 in FIG. 18). At the same time, the alignment result may be output in an outer memory (404 in FIG. 18) such as a hard disc.

Figure 4:
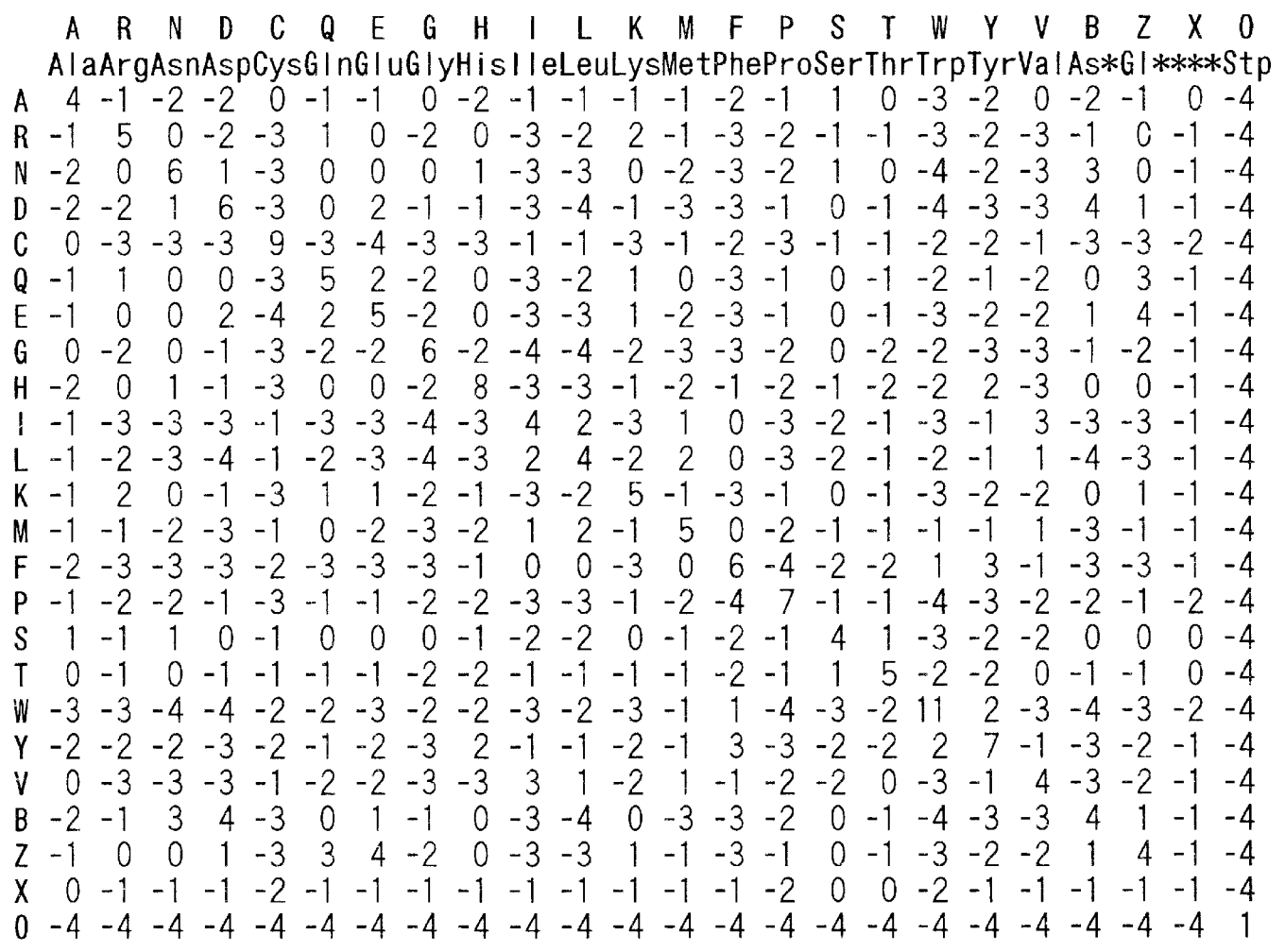

FIG. 4 shows Blosum 62, an example of table of prior art prescribing scores to be given to combinations of two amino acids which is used in the embodiment of the present invention. The symbols A, R, N, - - - , W, Y and V on the axis of abscissa and the axis of ordinate in FIG. 4 are abbreviations of amino acids. The symbol B (As*) denotes either Asn or Asp, the symbol Z (Gl*) denotes either Gln or Clu, the symbol X (***) denotes either incapability of translation or an unknown amino acid, and the symbol O (Stp) denotes a termination codon.

There is explained below a method for translating each of the query DNA base sequence and the target DNA base sequence read out of the DNA base sequence data base into an amino acid sequence in view of nucleotide insertions or depletions [(step 304) and (step 306)].

FIG. 5 shows a codon table of prior art prescribing the termination of translation into amino acids and the kinds of amino acids so that they may correspond to the triplet nucleotide units (codon units), respectively, in the codon table. In each of the DNA base sequences, each triplet nucleotide unit (codon) codes for an amino acid according to FIG. 5. In FIG. 5, the symbols in the parentheses are one-word abbreviations of amino acids.

Figure 6:
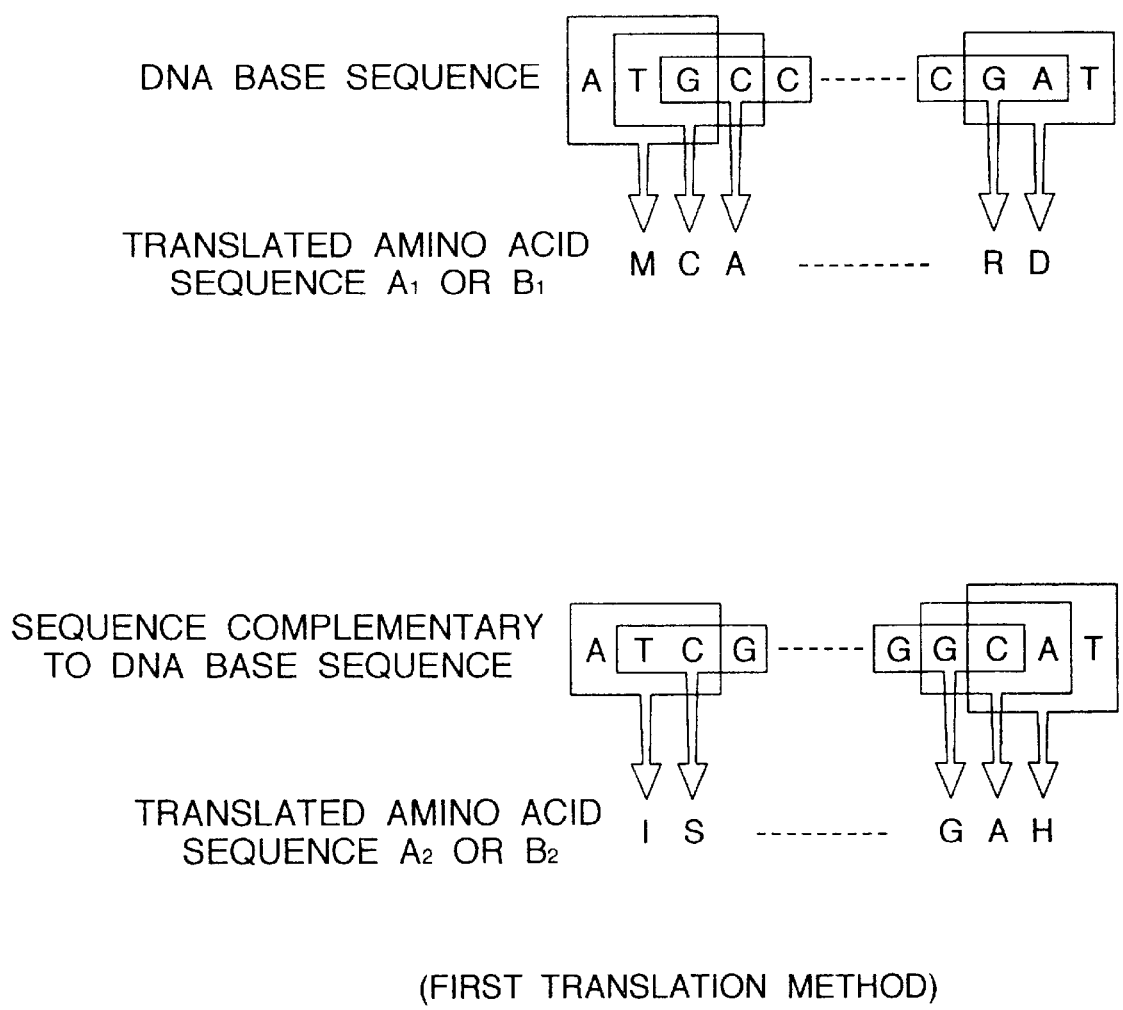
FIG. 6 is a diagram illustrating the first translation method for translating a DNA base sequence into an amino acid sequence in the embodiment of the present invention.

FIG. 6 is a diagram illustrating the first translation method for translating each DNA base sequence into an amino acid sequence in the embodiment of the present invention. In the first translation method, a codon (a triplet of nucleotides) is picked out from the 5'-terminal of each DNA base sequence and translated into an amino acid according to FIG. 5. Then, the next codon having a starting point one base after that of the first codon is picked out and translated into an amino acid according to FIG. 5. Thereafter, subsequent codons each having a starting point one base after that of the preceding codon are continuously translated in the same manner as above, until the last nucleotide of a codon picked out agrees with the nucleotide at the 3'-terminal of the DNA base sequence, whereby the DNA base sequence is translated into an amino acid sequence. Thus, the translated amino acid sequence $A_1$ or $B_1$ is obtained. A sequence complementary to the DNA base sequence is also translated into an amino acid sequence according to FIG. 5 in the same manner as above. Thus, the translated amino acid sequence $A_2$ or $B_2$ is obtained. Consequently, two kinds in all of the translated amino acid sequences ($A_1$ and $A_2$, or $B_1$ and $B_2$) can be obtained by the first translation method.

In FIG. 6, ATGCC, - - -, CGAT is chosen as an example of DNA base sequence. A codon ATG is picked out from the 5'-terminal and translated into an amino acid according to FIG. 5, and the next codon TGC having a starting point one base after that of the first codon is picked out and then translated into an amino acid according to FIG. 5. Thereafter, subsequent codons GCC, - - -, CGA and GAT each having a starting point one base after that of the preceding codon are picked out and then translated into amino acids A, - - -, R and D, respectively. The resulting translated amino acid sequence is MCA, - - -, RD. As shown in FIG. 6, a sequence complementary to the DNA base sequence ATCG, - - -, GGCAT is also translated into an amino acid sequence according to FIG. 5 in the same manner as above, whereby the translated amino acid sequence IS, - - -, GAH is obtained.

FIG. 7 is a diagram illustrating the second and third translation methods for translating each DNA base sequence into an amino acid sequence in the embodiment of the present invention.

In the second translation method, four nucleotides are picked out from the 5'-terminal of each DNA base sequence, and the second of the four nucleotides is taken as an inserted nucleotide. The remaining three nucleotides (a first revised DNA base sequence) are translated into an amino acid according to FIG. 5. Thereafter, the same translation is repeated according to FIG. 5 except for picking out subsequent quartets of successive nucleotides each of which has a starting point one base after that of the preceding quartet of successive nucleotides, until the last nucleotide of four successive nucleotides picked out agrees with the nucleotide at the 3'-terminal of the DNA base sequence, whereby the DNA base sequence is translated into an amino acid sequence. Thus, the translated amino acid sequence $A_3$ or $B_3$ is obtained.

In the third translation method, four nucleotides are picked out from the 5'-terminal of each DNA base sequence, and the third of the four nucleotides is taken as an inserted nucleotide. The remaining three nucleotides (a second revised DNA base sequence) are translated into an amino acid according to FIG. 5. Thereafter, the same translation is repeated according to FIG. 5 except for picking out subsequent quartets of successive nucleotides each of which has a starting point one base after that of the preceding quartet of successive nucleotides, until the last nucleotide of four successive nucleotides picked out agrees with the nucleotide at the 3'-terminal of the DNA base sequence, whereby the DNA base sequence is translated into an amino acid sequence. Thus, the translated amino acid sequence $A_4$ or $B_4$ is obtained.

A sequence complementary to each DNA base sequence is translated by each of the second and third translation methods in the same manner as above, whereby a translated amino acid sequence $A_5$ or $B_5$ and a translated amino acid sequence $A_6$ or $B_6$ are obtained which are not shown. Consequently, two kinds in all of the translated amino acid sequences ($A_3$ and $A_5$, or $B_3$ and $B_5$) can be obtained by the second translation method, and two kinds in all of the translated amino acid sequences ($A_4$ and $A_6$, or $B_4$ and $B_6$) can be obtained by the third translation method.

In the example shown in FIG. 7, the DNA base sequence is ATGCC, - - -, CGAT. Therefore, when the DNA base sequence is translated into an amino acid sequence by each of the second and third translation methods, four nucleotides corresponding to ATGC are picked out from the 5'-terminal at first, and AGC, a base sequence in the case of taking the second nucleotide (T) as an inserted nucleotide (a first revised DNA base sequence) and ATC, a base sequence in the case of taking the third nucleotide (G) as an inserted nucleotide (a second revised DNA base sequence) are translated into an amino acids S and I, respectively. Next, TCC (a first revised DNA base sequence) and TGC (a second revised DNA base sequence) which have been obtained from TGCC (i.e. a quartet of nucleotides having a starting point one base after that of the first quartet of nucleotides) are translated into an amino acids S and C, respectively. Thereafter, such translation is continued in the same manner as above except for picking out subsequent quartets of nucleotides each of which has a starting point one base after that of the preceding quartet of nucleotides, whereby amino acid sequences are translated from the DNA base sequence. Consequently, the translated amino acid sequences are SS, - - -, H and IC, - - -, R. In addition, ATCG, - - -, GGCAT, a sequence complementary to the DNA base sequence shown in FIG. 7 is translated into an amino acid sequence by each of the second and third translation methods in the same manner as above to obtain the translated amino acid sequences not shown.

There is explained below in detail (step 307) in which accumulated scores between translated amino acid sequences are calculated by the dynamic programming method for calculating accumulated similarities.

Figure 1:
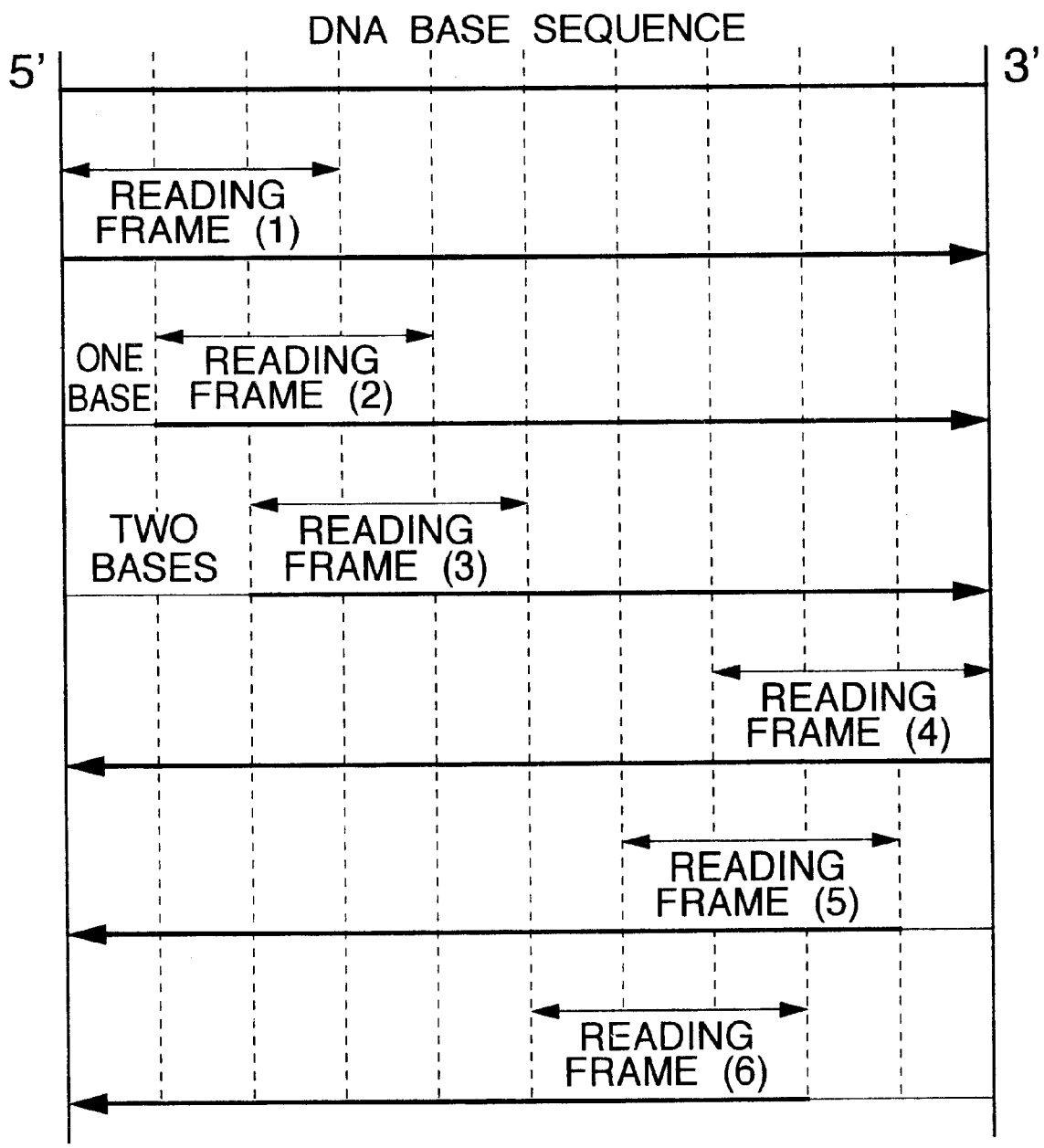
FIG. 1 is a diagram illustrating six kinds of reading frames of prior art in a DNA base sequence in the translation of the DNA base sequence into an amino acid sequence.
Figure 2:
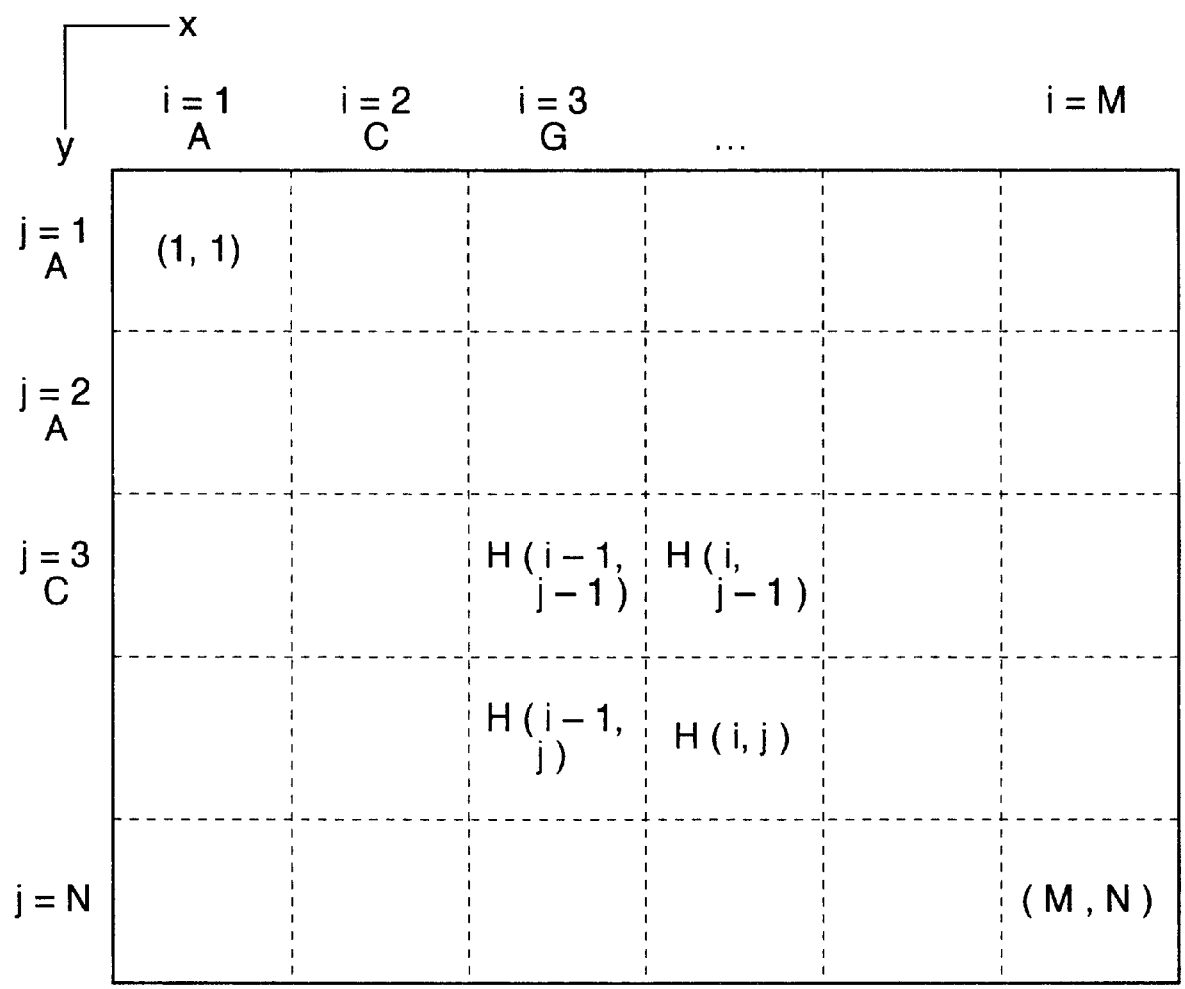
FIG. 2 is a diagram illustrating accumulation paths of scores for comparing DNA base sequences by the Smith-Waterman method, a prior art.

In the present invention, a score matrix for comparing amino acid sequences is obtained by modifying the score matrix for comparing DNA base sequences according to the Smith-Waterman method which is shown in FIG. 2. Using the score table prescribing scores to be given to combinations of two amino acids which is shown in FIG. 4, similarities between two amino acids of translated amino acid sequences, respectively, to be compared is determined and then accumulated. Accumulated similarities between the translated amino acid sequences are calculated by the dynamic programming method by using the translated amino acid sequences $A_1$, $A_2$, $A_3$, $A_4$, $A_5$ and $A_6$ obtained in (step 304) and the translated amino acid sequences $B_1$, $B_2$, $B_3$, $B_4$, $B_5$ and $B_6$ obtained in (step 306).

The bases of a first translated amino acid sequence ($A_1$ or $A_2$) are aligned in regular order along a first axis (for example, x-axis) from the 5'-terminal of the DNA base sequence corresponding to the first translated amino acid sequence, and the bases of a second translated amino acid sequence ($B_1$ or $B_2$) are aligned in regular order along a second axis (for example, y-axis) from the 5'-terminal of the DNA base sequence corresponding to the second translated amino acid sequence. Thus, there is formed a score matrix H in which the value H(i, j) of a score matrix element (i, j) indicate an accumulated similarity between an amino acid sequence from the first amino acid to the i-th amino acid in the first translated amino acid sequence and an amino acid sequence from the first amino acid to the j-th amino acid in the second translated amino acid sequence. The bases of a 1st, 3rd, 5th, 7th or 9th translated amino acid sequence (any of $A_1$, $A_2$, $A_3$, $A_4$, $A_5$ and $A_6$) are aligned in regular order along a first axis (for example, x-axis) from the 5'-terminal of the DNA base sequence corresponding to the 1st, 3rd, 5th, 7th or 9th translated amino acid sequence, and the bases of a 2nd, 4th, 6th, 8th or 10th translated amino acid sequence (any of $B_1$, $B_2$, $B_3$, $B_4$, $B_5$ and $B_6$) are aligned in regular order along a second axis (for example, y-axis) from the 5'-terminal of the DNA base sequence corresponding to the 2nd, 4th, 6th, 8th or 10th translated amino acid sequence. Thus, there are formed 1st, 2nd, 3rd, 4th and 5th matrices $s_1(i, j)$ to $s_5(i, j)$ which indicate the score (similarity) of each combination of two amino acids. First to fourth groups of 5 matrices each are formed by combination of the translated amino acid sequence $A_1$, $A_2$, $A_3$, $A_4$, $A_5$ or $A_6$ and the translated amino acid sequence $B_1$, $B_2$, $B_3$, $B_4$, $B_5$ or $B_6$. In each of the 5 matrices, the translated amino acid sequence along the first axis and that on the second axis are referred to as $A_i$ and $Bj$, respectively, and for simplification, the translated amino acid sequences along the first axis and the second axis, respectively, in each matrix is represented by $(A_i, B_j)$.

The 1st group of matrices is composed of a score matrix H having sequences $(A_1, B_1)$, a 1st matrix $s_1$ having sequences $(A_1, B_1)$, a 2nd matrix $s_2$ having sequences $(A_1, B_3)$, a 3rd matrix $s_3$ having sequences $(A_1, B_4)$, a 4th matrix $s_4$ having sequences $(A_3, B_1)$, and a 5th matrix $s_5$ having sequences $(A_4, B_1)$, wherein $A_1$ is used as the 1st, 3rd and 5th translated amino acid sequences, $A_3$ as the 7th translated amino acid sequence, $A_4$ as the 9th translated amino acid sequence, $B_1$ as the 2nd, 8th and 10th translated amino acid sequences, $B_3$ as the 4th translated amino acid sequence, and $B_4$ as the 6th translated amino acid sequence.

The 2nd group of matrices is composed of a score matrix H having sequences $(A_1, B_2)$, a 1st matrix $s_1$ having sequences $(A_1, B_2)$, a 2nd matrix $s_2$ having sequences $(A_1, B_5)$, a 3rd matrix $s_3$ having sequences $(A_1, B_6)$, a 4th matrix $s_4$ having sequences $(A_3, B_2)$, and a 5th matrix $s_5$ having sequences $(A_4, B_2)$, wherein $A_1$ is used as the 1st, 3rd and 5th translated amino acid sequences, $A_3$ as the 7th translated amino acid sequence, $A_4$ as the 9th translated amino acid sequence, $B_2$ as the 2nd, 8th and 10th translated amino acid sequences, $B_5$ as the 4th translated amino acid sequence, and $B_6$ as the 6th translated amino acid sequence.

The 3rd group of matrices is composed of a score matrix H having sequences $(A_2, B_1)$, a 1st matrix $s_1$ having sequences $(A_2, B_1)$, a 2nd matrix $s_2$ having sequences $(A_2, B_3)$, a 3rd matrix $s_3$ having sequences $(A_2, B_4)$, a 4th matrix $s_4$ having sequences $(A_5, B_1)$, and a 5th matrix $s_5$ having sequences $(A_6, B_1)$, wherein $A_2$ is used as the 1st, 3rd and 5th translated amino acid sequences, $A_5$ as the 7th translated amino acid sequence, $A_6$ as the 9th translated amino acid sequence, $B_1$ as the 2nd, 8th and 10th translated amino acid sequences, $B_3$ as the 4th translated amino acid sequence, and $B_4$ as the 6th translated amino acid sequence.

The 4th group of matrices is composed of a score matrix H having sequences $(A_2, B_2)$, a 1st matrix $s_1$ having sequences $(A_2, B_2)$, a 2nd matrix $s_2$ having sequences $(A_2, B_5)$, a 3rd matrix $s_3$ having sequences $(A_2, B_6)$, a 4th matrix $s_4$ having sequences $(A_5, B_2)$, and a 5th matrix $s_5$ having sequences $(A_6, B_2)$, wherein $A_2$ is used as the 1st, 3rd and 5th translated mino acid sequences, $A_5$ as the 7th translated amino acid sequence, $A_6$ as the 9th translated amino acid sequence, $B_2$ as the 2nd, 8th and 10th translated amino acid sequences, $B_5$ as the 4th translated amino acid sequence, and $B_6$ as the 6th translated amino acid sequence.

Figure 8:
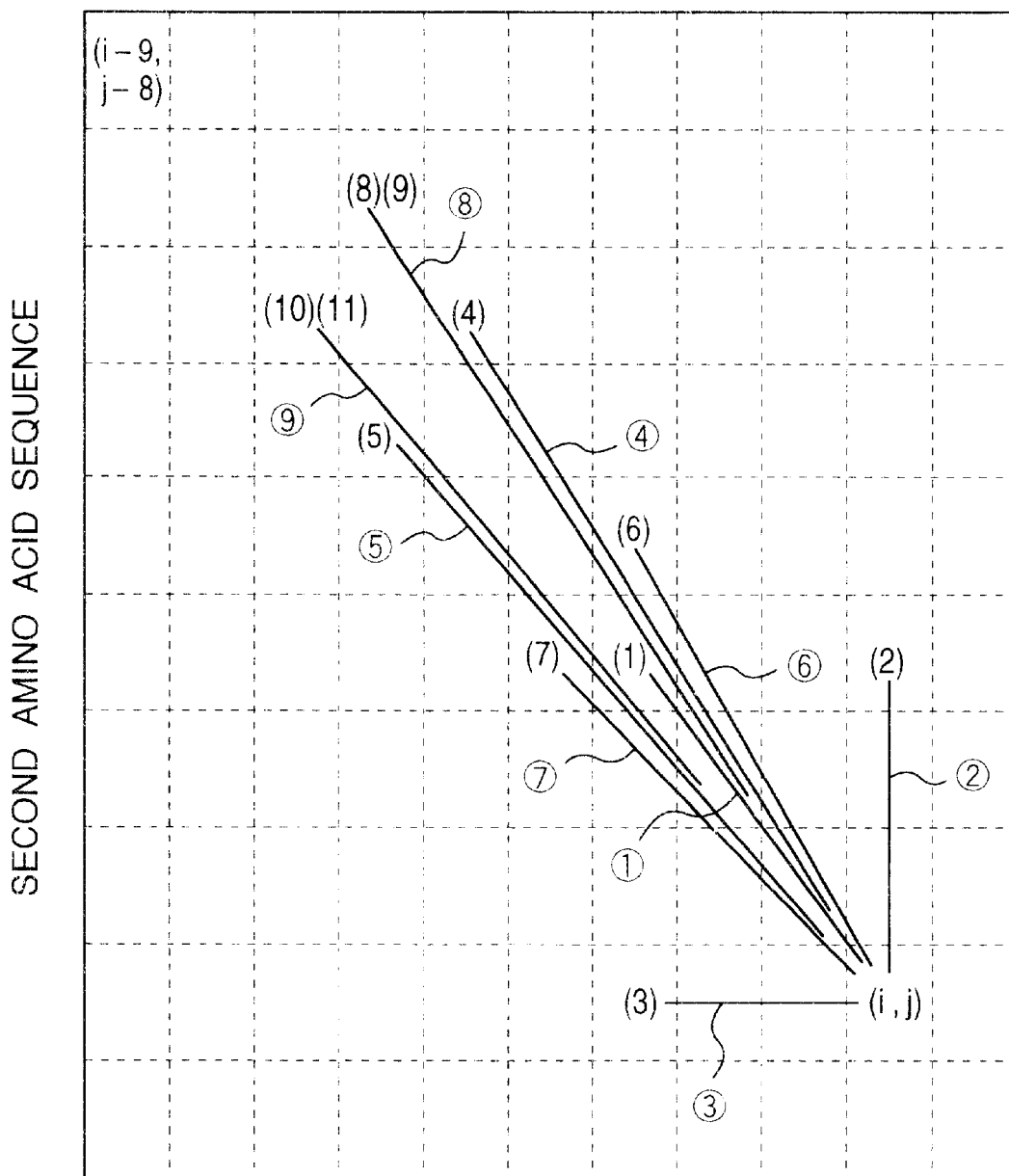
FIG. 8 is a diagram illustrating score accumulation paths for comparison of translated amino acid sequences in the embodiment of the present invention.

FIG. 8 is a diagram illustrating score accumulation paths for comparison of DNA base sequences in the embodiment of the present invention.

The 1st to 4th groups of matrices are independently used. The shift paths (search paths) ① to ⑨ in 9 directions to a score matrix element (i, j) shown in FIG. 8 are considered for each group of matrices by the dynamic programming method. The position of (i, j) is shifted toward the score matrix element (M, N) at the lower right corner in FIG. 8 from the score matrix element (1, 1) at the upper left corner by changing the number i from 1 to M (the number of amino acids constituting the amino acid sequence on the first axis of each score matrix) and the number j from 1 to N (the number of amino acids constituting the amino acid sequence on the second axis of the score matrix), whereby there is determined the optimum path (the optimum alignment) showing the optimum combination for similarity of each amino acid of the first translated amino acid sequence and a corresponding amino acid of the second translated amino acid sequence.

The value H(i, j) of a score matrix element (i, j) indicates an accumulated similarity between an amino acid sequence from the first amino acid to the i-th amino acid in the first translated amino acid sequence and an amino acid sequence from the first amino acid to the j-th amino acid in the second translated amino acid sequence.

In the case of the shift paths ① to ⑨ in the 9 directions to a point (i, j) from points (1) to (11) shown in FIG. 8, the maximum among $H_1(i, j)$ to $H_{11}(i, j)$ [(equation 16)] is selected as an accumulated similarity (score) H(i, j). For determining the scores $s_1(i, j)$ to $s_5(i, j)$, the score table shown in FIG. 4 is used. Each of $H_1(i, j)$ to $H_{11}(i, j)$ is defined by (equation 5) to (equation 15), respectively, by using the scores $s_1(i, j)$ to $s_5(i, j)$ which indicate similarities between the i-th amino acid in the amino acid sequence on the first axis and the j-th amino acid in the amino acid sequence on the second axis, gap penalty scores $W_a$ and $W_n$, and the values of score matrix elements at the original points before shift to the point (i, j), H(i−3, j−3), H(i−3, j), H(i, j−3), H(i−5, j−6), H(i−6, j−5), H(i−3, j−4), H(i−4, j−3), H(i−6, j−7) and H(i−7, j−6).

Each of FIG. 9 and FIG. 10 shows the relationship between the first term (i−6, j−7) of $H_8(i, j)$ or $H_9(i, j)$, respectively, and (i, j). Each of FIG. 11 and FIG. 12 shows the relationship between the first term (i−7, j−6) of $H_{10}(i, j)$ or $H_{11}(i, j)$, respectively, and (i, j). The point (i−3, j−4) in each of FIG. 9 and FIG. 10 is a point at which scores $s_2$ and $s_3$ are determined. The point (i−4, j−3) in each of FIG. 11 and FIG. 12 is a point at which scores $s_4$ and $s_5$ are determined.

$$H_1(i, j) = H(i-3, j-3) + s_1(i, j) = H(i-3, j-3) + s^*_1(A^*_i, B^*_j) \quad \text{(equation 5)}$$

wherein $H_1(i, j)$ corresponds to a shift path from a point (i−3, j−3) to a point (i, j).

$$H_2(i, j) = H(i, j-3) + w_a \quad \text{(equation 6)}$$

wherein $H_2(i, j)$ corresponds to a shift path from a point (i, j−3) to a point (i, j).

$$H_3(i, j) = H(i-3, j) + w_a \quad \text{(equation 7)}$$

wherein $H_3(i, j)$ corresponds to a shift path from a point (i−3, j) to a point (i, j).

$$H_4(i, j)=H(i-5, j-6)+w_n+s_1(i, j)=H(i-5, j-6)+w_n+s_1*(A*_i, B*_j) \quad \text{(equation 8)}$$

wherein $H_4(i, j)$ corresponds to a shift path from a point (i−5, j−6) to a point (i, j).

$$H_5(i, j)=H(i-6, j-5)+w_n+s_1(i, j)=H(i-6, j-5)+w_n+s_1*(A*_i, B*_j) \quad \text{(equation 9)}$$

wherein $H_5(i, j)$ corresponds to a shift path from a point (i−6, j−5) to a point (i, j).

$$H_6(i, j)=H(i-3, j-4)+w_n+s_1(i, j)=H(i-3, j-4)+w_n+s_1*(A*_i, B*_j) \quad \text{(equation 10)}$$

wherein $H_6(i, j)$ corresponds to a shift path from a point (i−3, j−4) to a point (i, j).

$$H_7(i, j)=H(i-4, j-3)+w_n+s_1(i, j)=H(i-4, j-3)+w_n+s_1(A*_i, B*j) \quad \text{(equation 11)}$$

wherein $H_7(i, j)$ corresponds to a shift path from a point (i−4, j−3) to a point (i, j).

$$H_8(i, j)=H(i-6, j-7)+w_n+s_2(i-3, j-4)+s_1(i, j)=H(i-6, j-7)+w_n+s_2*(A*_{i-3}, \{b_{j-4}b_{j-3}b_{j-1}\})+s_1*(A*_i, B*_j) \quad \text{(equation 12)}$$

$$H_9(i, j)=H(i-6, j-7)+w_n+s_3(i-3, j-4)+s_1(i, j)=H(i-6, j-7)+w_n+s_3*(A*_{i-3}, \{b_{j-4}b_{j-2}b_{j-1}\})+s_1*(A*_i, B*_j) \quad \text{(equation 13)}$$

wherein each of $H_8(i, j)$ and $H_9(i, j)$ involves a shift path from a point (i−6, j−7) to a point (i, j).

$$H_{10}(i, j)=H(i-7, j-6)+w_n+s_4(i-4, j-3)+s_1(i, j)=H(i-7, j-6)+w_n+s_4*(\{a_{i-4}a_{i-3}a_{i-1}\}, B*_{j-3})+s_1*(A*_i, B*_j) \quad \text{(equation 14)}$$

$$H_{11}(i, j)=H(i-7, j-6)+w_n+s_5(i-4, j-3)+s_1(i, j)=H(i-7, j-6)+w_n+s_5*(\{a_{i-4}a_{i-2}a_{i-1}\}, B*_{j-3})+s_1*(A*_i, B*_j) \quad \text{(equation 15)}$$

wherein each of $H_{10}(i, j)$ and $H_{11}(i, j)$ involves a shift path from a point (i−7, j−6) to a point (i, j).

$$H(i, j)=\max\{H_1(i, j), H_2(i, j), H_3(i, j), H_4(i, j), H_5(i, j), H_6(i, j), H_7(i, j), H_8(i, j), H_9(i, j), H_{10}(i, j), H_{11}(i, j)\} \quad \text{(equation 16)}$$

$$s_1(i, j)=s_1*(A*_i, B*_j) \quad \text{(equation 17)}$$

$$s_2(i-3, j-4)=s*(A*_{i-3}, \{b_{j-4}b_{j-3}b_{j-1}\}) \quad \text{(equation 18)}$$

$$s_3(i-3, j-4)=s*(A*_{i-3}, \{b_{j-4}b_{j-2}b_{j-1}\}) \quad \text{(equation 19)}$$

$$s_4(i-4, j-3)=s*(\{a_{i-4}a_{i-3}a_{i-1}\}, B*_{j-3}) \quad \text{(equation 20)}$$

$$s_5(i-4, j-3)=s*(\{a_{i-4}a_{i-2}a_{i-1}\}, B*_{j-3}) \quad \text{(equation 21)}$$

In the above equations, $A*_i$ is the i-th codon (triplet of nucleotides) of the first DNA base sequence [the query DNA base sequence (hereinafter referred to as A*)], $B*_j$ is the j-th codon (triplet of nucleotides) of the second DNA base sequence [the target DNA base sequence (hereinafter referred to as B*)], $a_i$ is the i-th nucleotide of A*, and $b_j$ is the j-th nucleotide of B*. The right member of each of (equation 17) to (equation 21) indicates a score between codons and hence can be determined according to the score table shown in FIG. 4, by translating each codon into an amino acid.

In the manner described above, the optimum path (the optimum alignment) showing the optimum combination for similarity of each amino acid of the first translated amino acid sequence and a corresponding amino acid of the second translated amino acid sequence is determined for each of the first to fourth groups of matrices by the dynamic programming method by using these groups of matrices independently.

In the above equations, $w_a$ denotes a gap penalty due to an amino acid insertion or deletion, and $w_n$ denotes a gap penalty due to a nucleotide insertion or deletion in the DNA base sequence. In the present embodiment, it was assumed that $w_a=w_n=-12$. When successive amino acid insertions or deletions are present, $w_a$ was taken as −12 at the first insertion or deletion and as −4 at the second and subsequent insertions or deletions.

There is given below a detailed explanation of (step 312) in which accumulated scores and paths are calculated by the dynamic programming method for obtaining alignment results, and (step 313) in which tracing of a path giving the maximum accumulated score is calculated.

In (step 312), the accumulated scores are determined by the dynamic programming method by carrying out the same calculation as described in (step 307), for two amino acid sequences giving top accumulated scores which have been obtained from the query DNA base sequence and the target DNA base sequence read out of the DNA base sequence data base, respectively. In this case, for each score matrix element, information on the kind of a calculation path selected from those represented by (equation 5) to (equation 16) and a shift path giving the maximum accumulated similarity (score) are stored as the position (i, j) of the final of the score matrix elements, in addition to the accumulated similarities (scores).

In (step 313), the calculation path stored for each score matrix element is traced back from the position (i, j) of the final of the score matrix elements giving the maximum accumulated similarity (score) which has been stored in (step 312), whereby there can be known an alignment result of the translated amino acid sequences which gives the maximum accumulated similarity (score).

FIG. 13 is a diagram showing general examples of alignment result which correspond to the shift paths, respectively, in the 9 directions in calculation by the dynamic programming method in the embodiment of the present invention.

FIG. 14 is a diagram showing specific examples of alignment result which correspond to shift paths, respectively, in the 9 directions in calculation by the dynamic programming method in the embodiment of the present invention.

In FIG. 14, the first line in each example of alignment represents a first DNA base sequence, the second line one or two amino acids translated from this first DNA base sequence, the third line one or two amino acids translated from a second DNA base sequence, and the fourth line this second DNA base sequence. The symbol "-" represents a nucleotide of amino acid deletion, and the symbol "*" represents an amino acid which cannot be determined by translation because of a nucleotide deletion or the presence of an unknown base n which has not been determined to be any of a, c, g and t.

Next, examples of practical application of the present embodiment is explained below. There was chosen a query sequence concerning *Arabidopsis thaliana* registered in the EST data base of Gen Bank, a public data base of DNA base sequences, and all sequences derived from rice (*Oriza sativa*) which had been registered in the EST data base were used as target sequences for similarity search. Each DNA base sequence registered in the EST data base involve a definite amount of sequence errors because the output result from a DNA sequencer has been registered as such. Therefore, such DNA base sequences are suitable for confirming the effectiveness of the present invention in which two DNA base sequences are compared through amino acid sequences in view of nucleotide insertions or deletions present in the DNA base sequences.

Each of FIG. 15, FIG. 16 and FIG. 17 is a diagram showing an example of alignment result obtained by similarity search in the embodiment of the present invention. In each of FIG. 15, FIG. 16 and FIG. 17, the "Query sequence" section shows a name given to a query DNA base sequence and a brief explanation of this sequence, and the "Target sequence" section shows a name given to a target DNA base sequence read out of the EST data base and selected by similarity search, and a brief explanation of this sequence. The "Score" section shows the accumulated similarity (score), the lengths of the query sequence and the target sequence, and the alignment regions of the query sequence and the target sequence.

In each "Query" section showing the alignment result, the query sequence and an amino acid sequence translated from the query sequence are shown in the upper row and the lower row, respectively. In each "Taget" section showing the alignment result, the target DNA base sequence selected by similarity search and an amino acid sequence translated from this DNA base sequence are shown in the lower row and the upper row, respectively.

The DNA base sequence and the translated amino acid sequence in the "Query" section showing the alignment result in FIG. 15 are represented by sequence numbers 1 and 2, respectively, and the translated amino acid sequence and the DNA base sequence in the "Taget" section showing the alignment result are represented by sequence numbers 3 and 4, respectively. The DNA base sequence and the translated amino acid sequence in the "Query" section showing the alignment result in FIG. 16 are represented by sequence numbers 5 and 6, respectively, and the translated amino acid sequence and DNA base sequence in the "Taget" section showing the alignment result are represented by sequence numbers 7 and 8, respectively. The DNA base sequence and the translated amino acid sequence in the "Query" section showing the alignment result in FIG. 17 are represented by sequence numbers 9 and 10, respectively, and the translated amino acid sequence and DNA base sequence in the "Taget" section showing the alignment result are represented by sequence numbers 11 and 12, respectively.

In FIG. 15, FIG. 16 and FIG. 17, the symbol: between the upper and lower translated amino acid sequences indicates that the amino acids corresponding to each other are the same . The symbol . between the sequences indicates that the value of a score matrix corresponding to the amino acids is positive. The absence of any symbol between the sequences indicates that the value of a score matrix corresponding to the amino acids is zero or negative. The symbol - represents a nucleotide or amino acid deletion. The symbol n denotes an unknown base n which has not been determined to be any of a, c, g and t. The symbol * denotes an amino acid which cannot be determined by translation because of the a nucleotide deletion or the presence of the unknown base.

The regions b, b', c, d and e shown by the quadrangles in FIG. 15 are explained below. Each of the regions b and b' indicate that the optimum path involves one or two amino acid insertions or deletions, i.e., a result corresponding to (equation 6) or (equation 7). The region c indicates that the optimum path involves a nucleotide deletion, i.e., a result corresponding to (equation 8) or (equation 9). Each of the regions d and e corresponds to a nucleotide insertion: the region d indicates that the optimum path involves a result corresponding to (equation 10) or (equation 11), and the region e indicates that the optimum path involves a result corresponding to any of (equation 12) to (equation 15).

Only the regions enclosed with the quadrangles in FIG. 16 and FIG. 17 are regions obtained by applying TBLASTX of prior art. In the method of the present invention, information on similarities between two base sequences can be obtained through translated amino acid sequences, in regions unobtainable by application of TBLASTX of prior art. Particularly when the result shown in FIG. 16 is compared with that obtained by the use of TBLASTX of prior art, it can be seen that the result obtained according to the present invention is information on the similarities in a continuous wider region. Particularly in the case of the example shown in FIG. 17, the method of the present invention gives information on the similarities in a region three times as wide as that obtained by TBLASTX of prior art.

In the present invention, since all of amino acid insertions or deletions and nucleotide insertions or deletions in each DNA base sequence are taken into consideration, similarity search can be carried out in a wide region of the base sequence to attain higher similarities (higher accumulated scores), so that an alignment result in the wide region of the base sequence can be obtained. Consequently, it becomes possible to obtain a more complete sequence as an amino acid sequence coded for by the DNA base sequence. Knowing the amino acid sequence of a protein coded for by a DNA base sequence is the first step in the analysis of the biological functions of genes. At present, the number of data in an available amino acid sequence data base is much smaller than that in an available DNA base sequence data base. Obtaining information on the amino acid sequence by the method of the present invention from the DNA base sequence obtained by measurement gives information useful for analyzing the function of the protein.

FIG. 18 is a diagram showing the structure of an apparatus for practicing the method for comparison of DNA base sequences of the present invention. The apparatus for practicing the method for comparison of DNA base sequences of the present invention comprises a device 401 for input of the above-mentioned first and second DNA base sequences; a calculation processing device 402 having the following programs within: a translation program for translating each DNA base sequence into an amino acid sequence, a sequence comparison program for comparing the above-mentioned first and second translated amino acid sequences, and a program for aligning the first and second translated amino acid sequences and aligning the DNA base sequences corresponding to the first and second, respectively, translated amino acid sequences; an output device for output of the maximum accumulated similarity, the alignment result of the first and second translated amino acid sequences, and the alignment result of the DNA base sequences corresponding to the first and second, respectively, translated amino acid sequences; and an outer memory which stores various DNA base sequence data bases, various amino acid sequence data bases, a score table, the codon table, etc.

A summary of the present invention is given below. The present invention is characterized by (A) a method for comparing DNA base sequences by comparing similaritie between a first DNA base sequence and a second DNA base sequence, which comprises (1) a step of dividing each of the first DNA base sequence and the second DNA base sequence into groups of successive three nucleotides each, translating each of these groups into an amino acid, and thereby obtaining a first amino acid sequence and a second amino acid sequence, respectively, (2) a step of determining similarities between each amino acid of the first translated amino acid sequence and each amino acid of the second translated amino acid sequence in view of nucleotide insertions or deletions in the first and second DNA base sequences and amino acid insertions or deletions in the first and second translated amino acid sequences, accumulating the thus determined similarities, and thereby determining a combination of each amino acid of the first translated amino acid sequence and a corresponding amino acid of the second translated amino acid sequence which gives the maximum accumulated similarity, (3) a step of outputting the maximum accumulated similarity, the alignment of the first and second translated amino acid sequences, the alignment of the first translated amino acid sequence and the first DNA base sequence, and the alignment of the second translated amino acid sequence and the second DNA base sequence, wherein the step (1) comprises translating each of the first and second DNA base sequences by each of the following methods: (i) a method of translating each DNA base sequence into an amino acid sequence while shifting a reading frame for the base sequence at every triplet of successive nucleotides base by base from the 5'-terminal of the base sequence, (ii) a method of shifting a reading frame for each DNA base sequence at every quartet of successive nucleotides base by base from the 5'-terminal of the base sequence, translating the three nucleotides other than the second nucleotide of each quartet into an amino acid, and thus translating the base sequence into an amino acid sequence, and (iii) a method of shifting a reading frame for each DNA base sequence at every quartet of successive nucleotides base by base from the 5'-terminal of the base sequence, translating the three nucleotides other than the third nucleotide of each quartet into an amino acid, and thus translating the base sequence into an amino acid sequence.

In the method (A), the present invention is characterized in that in the step (2), when a matrix is formed by aligning the amino acids of the first translated amino acid sequence in regular order in the direction of a first axis and the amino acids of the second translated amino acid sequence in regular order in the direction of a second axis, and an accumulated similarity at a matrix element (i, j) indicating the position of combination of the i-th amino acid of the first translated amino acid sequence and the j-th amino acid of the second translated amino acid sequence is determined, any path is selected from seven paths to the matrix element (i, j) from matrix elements (i−3, j−3), (i, j−3k), (i−3k, j), (i−3n+1, j−3n), (i−3n, j−3n+1), (i−3m, j−3m−1) and (i−3m−1, j−3m) [wherein k is an integer in a range of k≧1, m is an integer in a range of m≧1, n is an integer in a range of n≧2, i is an integer in a range of i≦M (M is the number of amino acids in the first translated amino acid sequence), and j is an integer in a range of j≦N (N is the number of amino acids in the second translated amino acid sequence)] so that the accumulated similarity may be maximum.

In addition, the present invention is characterized by (B) a method for comparing DNA base sequences by comparing similarities between a first DNA base sequence and a second DNA base sequence, which comprises (1) a step of dividing each of the first and second DNA base sequences into groups of successive three nucleotides each, translating each of these groups into an amino acid, and thereby obtaining a first amino acid sequence and a second amino acid sequence, respectively, (2) a step of determining similarities between each amino acid of the first translated amino acid sequence and each amino acid of the second translated amino acid sequence in view of nucleotide insertions or deletions in the first and second DNA base sequences and amino acid insertions or deletions in the first and second translated amino acid sequences, accumulating the thus determined similarities, and thereby determining a combination of each amino acid of the first translated amino acid sequence and a corresponding amino acid of the second translated amino acid sequence which gives the maximum accumulated similarity, (3) a step of outputting the maximum accumulated similarity, the alignment of the first and second translated amino acid sequences, the alignment of the first translated amino acid sequence and the first DNA base sequence, and the alignment of the second translated amino acid sequence and the second DNA base sequence.

Furthermore, the present invention is characterized in that each of the methods (A) and (B) comprises the same steps (1), (2) and (3) as above except for using a base sequence complementary to the first DNA base sequence in place of the first DNA base sequence and a base sequence complementary to the second DNA base sequence in place of the second DNA base sequence.

What is claimed is:

1. A method of comparing DNA base sequences between a first DNA base sequence having at least a first base, a second base, a third base, a fourth base, a fifth base and a sixth base in a direction toward 3'-end and a second DNA base sequence having at least a first base, a second base, a third base, a fourth base, a fifth base and a sixth base in a direction toward 3'-end comparing the steps of:

translating said first, third and fourth bases of said first sequence into a first amino acid, translating said first, third and fourth bases of said second sequence into a second amino acid, translating said second, fourth and fifth bases of said first sequence into a third amino acid, translating said second, fourth and fifth bases of said second sequence into a fourth amino acid, translating said third, fifth and sixth base of said first sequence into a fifth amino acid, translating said third, fifth and sixth base of said second sequence into a sixth amino acid, comparing said first amino acid and said second amino acid, comparing said third amino acid and said fourth amino acid, comparing said fifth amino acid and said sixth amino acid, and outputting the results of the comparing steps.

2. A method of comparing DNA base sequences between a first DNA base sequence having at least a first base, a second base, a third base, a fourth base, a fifth base and a sixth base in a direction toward 3'-end and a second DNA base sequence having at least a first base, a second base, a third base, a fourth base, a fifth base and a sixth base in a direction toward V-end comparing the steps of:

translating said first, second and fourth bases of said first sequence into a first amino acid, translating said first, second and fourth bases of said second sequence into a second amino acid, translating said second, third and fifth bases of said first sequence into a third amino acid, translating said second, third and fifth bases of said second sequence into a fourth amino acid, translating said third, fourth and sixth base of said first sequence into a fifth amino acid, translating said third, fourth and sixth base of said second sequence into a sixth amino acid, comparing said first amino acid and said second amino acid, comparing said third amino acid and said fourth amino acid, comparing said fifth amino acid and said sixth amino acid; and outputting the results of the comparing steps.

3. A method of comparing DNA base sequences between a first DNA base sequence having at least a first base, a second base, a third base, a fourth base and a fifth base in a direction toward 3'-end and a second DNA base sequence having at least a first base, a second base, a third base, a fourth base and a fifth base in a direction toward 3'-end comprising the steps of:

translating said first, second and third bases of said first sequence into a first amino acid;

translating said first, second and third bases of said second sequence into a second amino acid;

translating said second, third and fourth bases of said first sequence into a third amino acid;

translating said second, third and fourth bases of said second sequence into a fourth amino acid;

translating said third, fourth and fifth bases of said first sequence into a fifth amino acid;

translating said third, fourth and fifth bases of said second sequence into a sixth amino acid;

comparing said first amino acid and said second amino acid;

comparing said third amino acid and said fourth amino acid;

comparing said fifth amino acid and said sixth amino acid; and outputting the results of the comparing steps.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 254 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Arabidopsis thaliana (xi) SEQUENCE DESCRIPTION: SEQ ID NO:1:

```
TTCATTCATC CGTNGTTCCC CAGCTCCAAT CAGTCTCCGT TCCCTTCCAT CAGCCAACAC        60

ACAATCCCTC TTCGGTCTCA AATCAGGCAC CGCTCGTGGT GGACGTGTCA CAGCCATGGC       120

TACATACAAG GTCAAGTTCA TCACACCAGA AGGTGAGCTA GAGGTTGAGT GTGACGNCGN      180
```

```
CGTCTACGTT CTTNATGCTG CTGAGGAAGC TGGAATCGAT TTTGCCTTAC TCTTGCCGTG    240

CTGGTTCTTG TTCG                                                     254
```

(2) INFORMATION FOR SEQ ID NO:2:

(i) SEQUENCE CHARACTERISTICS:
        (A) LENGTH: 84 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Phe Ile His Pro Xaa Phe Pro Ser Ser Asn Arg Leu Arg Ser Leu Pro
1               5                   10                  15

Ser Ala Asn Thr Gln Ser Leu Phe Gly Leu Lys Ser Gly Thr Ala Arg
            20                  25                  30

Gly Gly Arg Val Thr Ala Met Ala Thr Tyr Lys Val Lys Phe Ile Thr
            35                  40                  45

Pro Glu Gly Glu Leu Glu Val Glu Cys Asp Xaa Xaa Val Tyr Val Leu
50                  55                  60

Xaa Ala Ala Glu Glu Ala Gly Ile Ile Leu Pro Tyr Ser Cys Arg Ala
65                  70                  75                  80

Gly Ser Cys Ser
```

(2) INFORMATION FOR SEQ ID NO:3:

(i) SEQUENCE CHARACTERISTICS:
        (A) LENGTH: 87 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Phe Leu Asn Pro Ala Arg Pro Leu Leu Arg Arg Pro Arg Ala Leu Pro
1               5                   10                  15

Ser Leu Val Thr Gln Ser Lys His Xaa Asn Met Ser Gly Leu Arg Ile
            20                  25                  30

Ser Asn Lys Phe Arg Val Ser Ala Thr Gly Xaa His Lys Val Lys Leu
            35                  40                  45

Ile Gly Pro Asp Gly Val Glu His Glu Phe Glu Ala Pro Glu Asp Thr
50                  55                  60

Tyr Ile Leu Glu Ala Ala Glu Thr Ala Gly Val Xaa Leu Pro Xaa Xaa
65                  70                  75                  80

Cys Arg Ala Gly Ser Cys Ser
                85
```

(2) INFORMATION FOR SEQ ID NO:4:

(i) SEQUENCE CHARACTERISTICS:
        (A) LENGTH: 260 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Oryza sativa (xi) SEQUENCE DESCRIPTION: SEQ ID NO:4:

```
TTCCTAAACC CGGCGCGGCC ATTGCTCCGG CGACCAAGAG CCCTTCCTTC ATTGGTTACG     60

CAAAGCAAAC ATTGAACATG TCAGGCCTAA GGATCTCCAA CAAGTTCAGG GTGTCCGCGA    120

CAGGTNGTCA CAAGGTAAAG CTTATAGGCC CGGACGGTGT CGAGCACGAG TTTGAAGCCC    180

CTGAAGATAC CTACATTCTC GAGGCCGCTG AAACTGCCGG GGTGGNGCTG CCATTNTNAT    240

GCCGTGCTGG ATCATGCTCC                                                260
```

(2) INFORMATION FOR SEQ ID NO:5:

(i) SEQUENCE CHARACTERISTICS:
        (A) LENGTH: 258 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Arabidopsis thaliana (xi) SEQUENCE DESCRIPTION: SEQ ID NO:5:

```
ATGGCGAATT CCGGCGAAGA GAAGTTGAAG CTCTACTCTT ACTGGAGAAG CTCGTGTGCT     60

CATCGTGTCC GTATCGCCCT CGCTTTGAAA GGGCTTGATT ATNAGTATAT ACCAGTGAAT    120

TTNCTCAAGG GTGATCAATT CGATTCANAT TTCAAGAAGA TCAATCCAAT GGGAACTGTA    180

CCAGCTCTGG TGGATGGAGA TGTTGTGATT AATGATTCTT TTGCGATAAT AATGTATCTG    240

GATGAGAAGT ACCCTGAG                                                   258
```

(2) INFORMATION FOR SEQ ID NO:6:

(i) SEQUENCE CHARACTERISTICS:
        (A) LENGTH: 86 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Ala Asn Ser Gly Glu Glu Lys Leu Lys Leu Tyr Ser Tyr Trp Arg
 1               5                  10                  15

Ser Ser Cys Ala His Arg Val Arg Ile Ala Leu Ala Leu Lys Gly Leu
            20                  25                  30

Asp Tyr Xaa Tyr Ile Pro Val Asn Xaa Leu Lys Gly Asp Gln Phe Asp
        35                  40                  45

Ser Xaa Phe Lys Lys Ile Asn Pro Met Gly Thr Val Pro Ala Leu Val
    50                  55                  60

Asp Gly Asp Val Val Ile Asn Asp Ser Phe Ala Ile Ile Met Tyr Leu
65                  70                  75                  80

Asp Glu Lys Tyr Pro Glu
                85
```

(2) INFORMATION FOR SEQ ID NO:7:

(i) SEQUENCE CHARACTERISTICS:
        (A) LENGTH: 83 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met Ala Gly Ser Gly Asp Glu Leu Met Leu Leu Gly Lys Trp Pro Ser
1               5                   10                  15

Pro Phe Val Thr Arg Val Glu Leu Ala Leu Gly Leu Lys Gly Leu Ser
                20                  25                  30

Tyr Glu Tyr Val Lys Gln Asp Leu Val Asn Lys Ser Glu Leu Leu Leu
            35                  40                  45

Ala Ser Asn Pro Val His Lys Lys Ile Pro Val Leu Ile His Asn Gly
        50                  55                  60

Lys Pro Val Cys Glu Ser Ser Ile Ile Val Gln Tyr Ile Asp Glu Ala
65                  70                  75                  80

Phe Pro Asp (2) INFORMATION FOR SEQ ID NO:8:

(i) SEQUENCE CHARACTERISTICS:
        (A) LENGTH: 249 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Oryza sativa (xi) SEQUENCE DESCRIPTION: SEQ ID NO:8:

ATGGCCGGAT CAGGAGACGA GCTGATGCTG CTCGGCAAAT GGCCAAGCCC ATTCGTCACC        60

AGGGTTGAGC TCGCGCTCGG CCTCAAGGGC CTCAGCTACG AGTACGTCAA GCAGGACCTC       120

GTCAACAAGA GCGAGCTCCT CCTCGCCTCC AACCCGGTGC ACAAGAAGAT CCCCGTGCTC       180

ATCCACAACG GCAAGCCGGT CTGCGAGTCG TCAATCATCG TGCAGTACAT CGACGAGGCC       240

TTCCCCGAC                                                              249

(2) INFORMATION FOR SEQ ID NO:9:

(i) SEQUENCE CHARACTERISTICS:
        (A) LENGTH: 186 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Arabidopsis thaliana (xi) SEQUENCE DESCRIPTION: SEQ ID NO:9:

GGAAGAGCTC CATGCTGCGA CAAGGCAAAC NTGAAGAAAG GACCATGGTC ACCGGAAGAN        60

GATGTGAAGC TCAAGGTTTA CATCGACAAA TATGGCACTG GTGGCAACTG GTTCGCACTG       120

CCTCAGAAAN TTGGNCTGAA GAGATGTGGT AAGANTTGCA GACTGAGATG GCTTAATTNC       180

TTAAGA                                                                 186

(2) INFORMATION FOR SEQ ID NO:10:

(i) SEQUENCE CHARACTERISTICS:
        (A) LENGTH: 62 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Gly Arg Ala Pro Cys Cys Asp Lys Ala Asn Xaa Lys Lys Gly Pro Trp
1               5                   10                  15

Ser Pro Glu Xaa Asp Xaa Glu Ala Gln Gly Leu His Arg Gln Ile Trp
            20              25                  30

His Trp Trp Gln Leu Val Arg Leu Pro Gln Lys Xaa Xaa Leu Lys Arg
        35              40                  45

Cys Gly Lys Xaa Cys Arg Leu Arg Trp Leu Asn Xaa Leu Arg
50              55                  60
```

(2) INFORMATION FOR SEQ ID NO:11:

(i) SEQUENCE CHARACTERISTICS:
        (A) LENGTH: 62 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Gly Arg His Ser Cys Cys Tyr Lys Gln Lys Leu Arg Lys Gly Leu Trp
1               5                   10                  15

Ser Xaa Glu Glu Asp Glu Glu Ala His Gly Pro His Asn Gln Ala Trp
            20              25                  30

Xaa Trp Leu Leu Gly His Arg Phe Gln Asn Leu Gln Gly Phe Gln Arg
        35              40                  45

Cys Ala Lys Ala Phe Arg Leu Arg Trp Xaa Asn Tyr Leu Arg
50              55                  60
```

(2) INFORMATION FOR SEQ ID NO:12:

(i) SEQUENCE CHARACTERISTICS:
        (A) LENGTH: 188 base pairs
        (B) TYPE: nucleic acid
        (C) STRANDEDNESS: both
        (D) TOPOLOGY: linear (ii) MOLECULE TYPE: cDNA to mRNA (vi) ORIGINAL SOURCE:
        (A) ORGANISM: Oryza sativa (xi) SEQUENCE DESCRIPTION: SEQ ID NO:12:

```
GGGAGACATT CCTGCTGCTA CAAGCAGAAG CTGAGGAAGG GGCTCTGGTC ANCTGAGGAG      60
GATGAGGAAG CTCATGGACC ACATAACCAA GCATGGNCAT GGCTGCTGGG GCACCGTTTC     120
CAAAACTTGC AGGGGTTTCA GAGATGTNGC AAAAGCTTTC AGGCTGAGGT TGGGTNAACT     180
ACTTGAGG                                                              188
```